US011978558B1

(12) United States Patent
Drakos

(10) Patent No.: US 11,978,558 B1
(45) Date of Patent: May 7, 2024

(54) PREDICTIVE DIAGNOSTIC INFORMATION SYSTEM

(71) Applicant: Nicholas D. P. Drakos, Southern Pines, NC (US)

(72) Inventor: Nicholas D. P. Drakos, Southern Pines, NC (US)

(73) Assignee: Hunamis, LLC, Southern Pines, NC (US)

( * ) Notice: Subject to any disclaimer, the term of this patent is extended or adjusted under 35 U.S.C. 154(b) by 259 days.

(21) Appl. No.: 17/125,720

(22) Filed: Dec. 17, 2020

(51) Int. Cl.
*G16H 50/20* (2018.01)
*G06F 18/214* (2023.01)
*G06N 5/043* (2023.01)
*G06T 7/00* (2017.01)
*G06T 7/246* (2017.01)

(52) U.S. Cl.
CPC ........... *G16H 50/20* (2018.01); *G06F 18/214* (2023.01); *G06N 5/043* (2013.01); *G06T 7/0012* (2013.01); *G06T 7/246* (2017.01); *G06T 2207/10048* (2013.01); *G06T 2207/30041* (2013.01); *G06T 2207/30076* (2013.01)

(58) Field of Classification Search
CPC ...... G16H 50/20; G06K 9/6256; G06N 5/043; G06T 7/0012; G06T 7/246; G06T 2207/10048; G06T 2207/30041; G06T 2207/30076
See application file for complete search history.

(56) References Cited

U.S. PATENT DOCUMENTS

| 10,568,526 | B2 | 2/2020 | McKenna et al. | |
|---|---|---|---|---|
| 10,667,723 | B2 | 6/2020 | Jacquel et al. | |
| 2018/0078158 | A1* | 3/2018 | Pekander | A61B 5/02141 |
| 2018/0103859 | A1* | 4/2018 | Provenzano | A61B 5/681 |
| 2018/0199870 | A1 | 7/2018 | Lee et al. | |

(Continued)

OTHER PUBLICATIONS

Agrawal, Ankit et al., "The Next Generation of Human-Drone Partnerships: Co-Designing an Emergency Response System," ACM, arXiv:2001.03849v1 [cs.HC], dated Jan. 12, 2020, 13 pages.

(Continued)

*Primary Examiner* — Siamak Harandi
(74) *Attorney, Agent, or Firm* — Davis Graham & Stubbs LLP

(57) ABSTRACT

A Predictive Diagnostic Information Capability-Technology (PreDICT™) system (100) enables users including expert and nonexpert users to provide information regarding a condition of a subject and receive timely and accurate information regarding risk stratification, treatment options and other medical evaluation information. The illustrated system (100) generally includes a user device (102) for use by a user assisting a subject (104), a processing platform (108), and a network (106) for connecting the user device (102) to the processing platform (108). The system (100) may also involve an emergency response network (130) that includes public-safety answering points (PSAPs) (132). The processing platform (108) processes the sensor information and other information from the user device (102), determines risk stratification information as well as medical diagnosis and treatment option information based on machine learning technology, and provides output information to the user device to assist the user in treating the subject (104).

31 Claims, 13 Drawing Sheets

(56) References Cited

U.S. PATENT DOCUMENTS

2019/0110754 A1 4/2019 Rao et al.
2020/0268281 A1 8/2020 Jacquel et al.
2020/0395126 A1* 12/2020 Walker .................. G16H 50/20
2021/0400211 A1* 12/2021 Galitz ................... A61B 5/445

OTHER PUBLICATIONS

Ahuja, Abhimanyu S., "The Impact of Artificial Intelligence in Medicine on the Future Role of the Physician," PeerJ, Chalres E. Schmidt College of Medicine, Florida Atlantic University, Boca Raton, FL USA, published Oct. 4, 2019, 19 pages.

Antink, Christoph Hoog et al., "A Broader Look: Camera-Based Vital Sign Estimation Across the Spectrum," Medical Information Technology (MedIT), Helmholtz-Institute for Biomedical Engineering, RWTH Aachen University, Aachen, Germany, published Aug. 16, 2019, 13 pages.

Drakos, Nicholas D., MD, "Chapter 19: Emergency Medicine Combat Lessons Learned," Blast Text Chapter, 16 pages. Year: 2020.

Kline, Jeffrey A. et al., "Decreased Facial Expression Variability In Patients withSerious Cardiopulmonary Disease in the Emergency Care Setting," Emerg Med J: first published as 10.1136/emermed-2014-203602 on Jul. 14, 2014, 6 pages.

Nadler, Roy et al., "The Value of Noninvasive Measurement of the Compensatory Reserve Index in Monitoring and Triage of Patients Experiencing Minimal Blood Loss," SHOCK, vol. 42, No. 2, pp. 93-98, 2014, 6 pages.

Papangelou, Alexander MD et al., "Automated Pu;illometry and Detection of Clinical Transtentorial Brain Herniation: A Case Series," Military Medicine, 183, 1/2:3113, 2018, 9 pages.

Patil, Omkar R. et al., "CamBP: A Camera-Based, Non-Contact Blood Pressure Monitor," ResearchGate Conference Paper, UBICOMP/ISWC '17 ADJUNCT, dated Sep. 11-15, 2017, Maui, Hawaii USA, 7 pages.

Lin, Shen et al., "Feasibility of Using Deep Learning to Detect Coronary Artery Disease Based on Facial Photo," ESC European Society of Cardiology, European Heart Journal (2020) 41, 4400-4411, Clinical Research Ischaemic Heart Disease, Dec. 22, 2020, 12 pages.

Wu, Hao-Yu et al., "Eulerian Video Magnification for Revealing Subtle Changes in the World," MIT SCAIL1, Quanta Research Cambridge, Inc., 8 pages.

* cited by examiner

DATA COLLECTION, CORRELATION and MODEL TRAINING

*NOTE: Model development and improvement may require multiple cycles through the process represented by this schematic For selected medical risk phenotypes, patients will be recorded or will record themselves

DATA ACQUISITION

| Non-Contact Data Acquisition | | Other Data Acquisition | Standard Of Care (SoC) Data Acquisition |
|---|---|---|---|
| Video | Audio | Motor/other | |
| Visible light, low light, Red-Blue-Green (RBG), and infrared Thermography (IRT) video collection of: The Subject- Bodily areas of interest to acquire the following parameters and variability thereof. <ul><li>Temperature</li><li>Skin color/perfusion/ moisture/lesions/wounds/ blood/other abnormalities</li><li>Respiratory action</li><li>Facial action units</li><li>Eye movements and blink rate</li><li>Pupillometry/Eye abnormalities- injection, discharge, etc</li><li>Posture, movement, gait, joint function, and motor coordination</li></ul> | The Subject- <ul><li>Vocal biomarkers related to articulation, speech patterns, tone, rate, and variability thereof</li></ul> The Subject and Environment- <ul><li>Specific words, phrases, or word/phrase patterns</li></ul> The Environment- <ul><li>Acoustic patterns and signatures related to geo-</li></ul> | The Subject- <ul><li>Touchscreen and/or other fine motor inputs to evaluate fine motor coordination and variability thereof</li><li>Wearable health/wellness/medical monitoring devices</li><li>Gyroscopic data to monitor gait and other motor characteristics</li><li>Accelerometer/impact monitors incorporated in sports or military helmets or otherwise worn or incorporated on a person, means of conveyance, or other location</li><li>Electronic stethoscope and/or ultrasound device to capture cardiac, pulmonary, and/or other auditory, motion, and internal structure data</li><li>Continuous glucose monitor (CGM) devices</li><li>Implanted cardiac pacemakers and defibrillators</li></ul> | History and Physical Exam: <ul><li>HPI, PM/S Hx, Physical Exam findings</li><li>Vital Signs</li></ul> Diagnostic Studies: <ul><li>EKG and telemetry</li><li>Laboratory studies (Blood, Urine, CSF, etc.)</li><li>Radiology studies- Xray, CT, U/S, MRI, etc.</li><li>Coronary patency evaluation- Treadmill, Coronary CT, PCI studies</li><li>Surgical Findings</li><li>Pathology or autopsy findings</li><li>Standardized screening/ clinical decision tools and models</li></ul> |

FIG. 3A

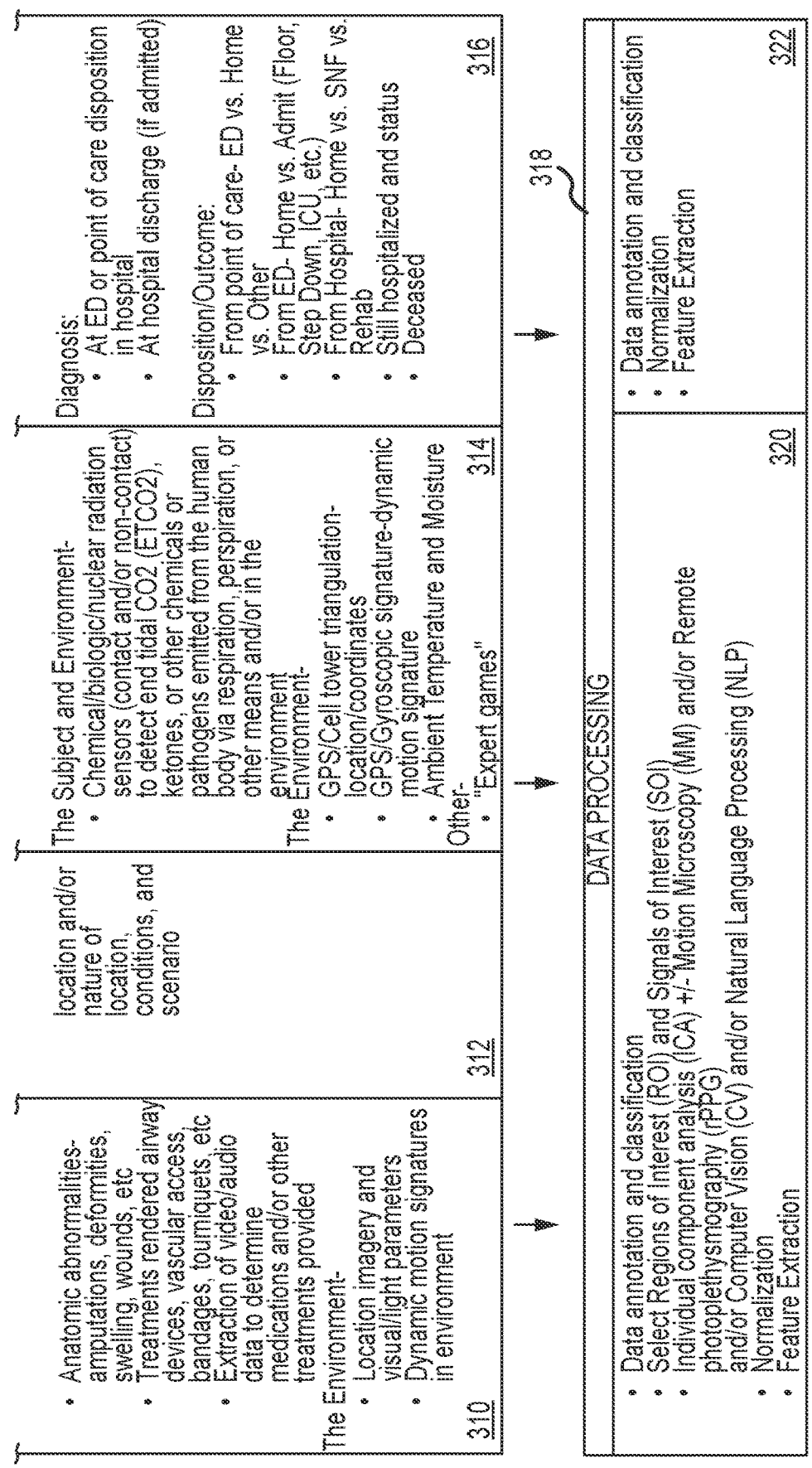

PreDICT MODEL DEPLOYMENT

For selected medical risk phenotypes patients will be recorded on record themselves

DATA ACQUISITION

| Non-Contact Data | | (+/-) Contact and Other Data |
|---|---|---|
| Video | Audio | |

Video (408):

Visible light, low light, Red-Blue-Green (RBG), and infrared Thermography (IRT) video collection of:

The Subject-
Bodily areas of interest to acquire the following parameters and variability thereof:
- Temperature
- Skin color/perfusion/moisture/lesions/wounds/blood/other abnormalities
- Respiratory action
- Facial action units
- Eye movements and blink rate
- Pupillometry/Eye abnormalities injection, discharge, etc.
- Posture, movement, gait, joint function, and motor coordination
- Anatomic abnormalities- amputations, deformities, swelling, wounds, etc.
- Treatments rendered- airway devices, vascular access, bandages, tourniquets, etc.
- Extraction of video/audio data to determine medications and/or other treatments provided The Environment-
- Location imagery and visual/light parameters
- Dynamic motion signatures in environment

Audio (410):

The Subject-
- Vocal biomarkers related to articulation, speech patterns, tone, rate, and variability thereof Subject and Environment-
- Specific words, phrases, or word/phrase patterns The Environment-
- Acoustic patterns and signatures related to geo-location and/or nature of location, conditions, and scenario

Contact and Other Data (412):

The Subject-
Contact-Non-invasive (CNI):
- Touch screen
- Gyroscopic
- Accelerometer/impact monitors
- Health/Wellness/Medical wearable devices
- Standard-of-Care CNI inputs
- Chemical/Biological/nuclear radiation sensors (contact/non-contact)
- Electronic stethoscope and/or ultrasound devices
- Continuous glucose monitor (CGM) devices
- Implanted cardiac pacemakers and defibrillators Contact-Non-invasive (CI):
- Standard-or-Care CI inputs The Environment-
- GPS/Cell tower triangulation- location/coordinates
- GPS/Gyroscopic signature- dynamic motion signature
- Ambient Temperature and Moisture

FIG. 4A

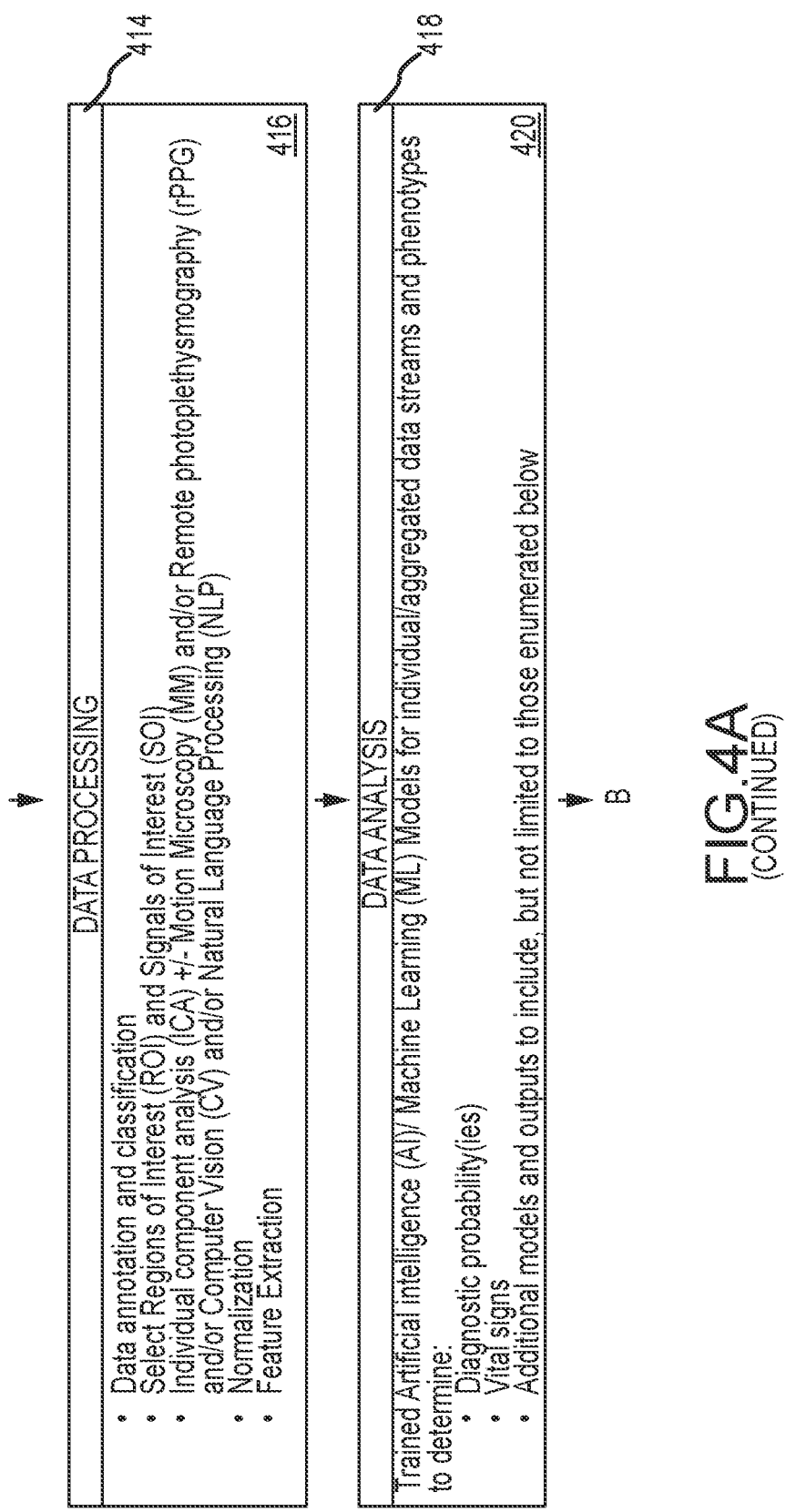

DATA PROCESSING (414)
- Data annotation and classification
- Select Regions of Interest (ROI) and Signals of Interest (SOI)
- Individual component analysis (ICA) +/- Motion Microscopy (MM) and/or Remote photoplethysmography (rPPG) and/or Computer Vision (CV) and/or Natural Language Processing (NLP)
- Normalization
- Feature Extraction

416

DATA ANALYSIS (418)

Trained Artificial Intelligence (AI)/ Machine Learning (ML) Models for individual/aggregated data streams and phenotypes to determine:
- Diagnostic probability(ies)
- Vital signs
- Additional models and outputs to include, but not limited to those enumerated below

PREDICTIVE ANALYTIC MODELS AND OUTPUTS — 422

Non-contact/Minimal-Contact diagnostic model — 424

Potential Outputs-

Diagnostic: Expressed with statistical confidence and/or representations thereof 1) Presence/absence of Illness/Injury
2) Presence/absence of a specific Illness/Injury
3) Probability distribution of possible Illness/Injury
4) Any of 1-3 with recommendations for follow-on action to improve diagnostic statistics and accuracy Including: Repeat/continued NCPA monitoring and/or Acquisition of non-invasive contact data (Touch screen, EKG/Telemetry, Ultrasound/echocardiogram, etc.) and/or Acquisition of invasive contact data (Blood or laboratory tests, Biopsy, etc.)

Therapeutic: The described diagnostic capability can be linked with existing medical reference databases or tests and/or can utilize machine learning (ML) and/or Artificial Intelligence (AI) capabilities to determine the most appropriate therapeutic cause(s) of action (COA) once a diagnosis is made and recommend this COA(s) to the user based on their level of expertise and current context (ie. Is the user a patient at home, a physician stopped at the scene of a traffic accident, or a physician in an emergency department, etc.)

426

- Non-contact vital signs model (Temp, HR, RR, BP, SPO2, STO2)
- Non-contact EKG and cardiac function monitoring
- Non-contact dimensional measurements
- Non/Minimal contact sensor for blood glucose monitoring and control and/or interface with continuous glucose monitor (CGM) device to optimize blood glucose monitoring and control

428

- SOC data (history, physical, laboratory, radiographic, and/or other data) Interpretation
- Multi-Sensor Scribe Patient "Fingerprint" consisting of some/all of the following data: Videographic, Audiographic, Physiologic, Anatomic, Radiographic, Gyroscopic, Touch, Motion, Chemical
- Context: Location, Motion, Ambient light and meteorological conditions, human factors and threats, Dynamic vs Static environment/conditions
- Recommend diagnostic and therapeutic interventions and courses of action

FIG. 4B

PREDICTIVE DIAGNOSTIC INFORMATION SYSTEM

FIELD OF THE INVENTION

The present invention relates generally to diagnostic evaluation and risk stratification in various medical and non-medical contexts, including for medical evaluation in time constrained critical illness or injury (TCCI) contexts and, in particular, to a system for enabling expert and nonexpert users to provide sensor and other input information and obtain rapid and accurate output information concerning a diagnosis and course of treatment.

BACKGROUND OF THE INVENTION

In many cases, decision-making and response could be improved by quick access to accurate information concerning risk stratification and diagnosis. In medical contexts, this includes situations where a patient is cared for by an expert in a medical facility, experts or non-experts in out-of-hospital settings, and situations where an individual is cared for by a non-expert or layperson, e.g., in an emergency setting. In the case of care by experts, ready access to such information could reduce misdiagnosis and decrease time to diagnosis. It is estimated that medical misdiagnosis, in the form of inaccurate, late, or delayed diagnoses, contribute to 40,000-80,000 American deaths per year. Moreover, it has been estimated that diagnostic errors and related inefficiencies cost the US economy $750 billion each year. Accordingly, improving medical diagnosis would have a substantial impact on lives as well as the economy.

The case of coronary care is illustrative. Approximately 8 to 10 million patients in US complain of chest pain annually. In most cases, the cause of the chest pain is benign but some patients have serious life-threatening conditions. Substantial amounts of healthcare resources are devoted to discriminating between these two groups of patients. The ideal solution would perfectly sort emergency department patients presenting with chest pain potentially indicative of acute coronary syndromes (ACS) into those who require further evaluation and treatment and those who can be safely discharged home. Unfortunately, sorting these patients is difficult given the limitations of available resources and errors occur.

The limitations are even more pronounced in certain emergency settings. In such cases, initial treatment decisions may be made by first responders or even laymen. These initial decisions often have a substantial impact on morbidity and mortality. The initial care providers may have limited knowledge and experience concerning the medical conditions that are presented and may also have limited equipment and resources to address the medical conditions. Even if the initial care provider can quickly establish communications with an expert, the ability of the expert to evaluate risks and prescribe an appropriate course of initial treatment from a remote location may be severely limited. As a result, subjects in emergency medical settings may receive inadequate or improper treatment despite the best of intentions.

SUMMARY OF THE INVENTION

The present invention is directed to an evaluation system and associated functionality for assisting in risk stratification and diagnosis that is useful in medical and non-medical environments. This system is particularly beneficial in connection with time-constrained, critical illness or injury (TCCI) settings where there is a great need for rapid identification of an initial course of treatment and the consequences of misdiagnosis can be severe. However, in a broad range of environments, the invention provides an augmented intelligence, predictive analytic diagnostic and therapeutic capability to improve diagnostic accuracy and efficiency by decreasing the time, risk, and resources required to risk-stratify patients and/or achieve diagnosis. In addition, the invention improves therapeutic efficiency by recommending and/or performing the most risk and time efficient interventions and/or courses of action in the prevailing risk-context.

In the TCCI context, initial decision-making centers around two goals: 1) addressing immediate threats to life, and 2) determining multiple treatment plans. Decisions about treatments require observations (evidence), but observations take time and resources. The key is identifying the best trade-off. The present invention facilitates these goals by enabling caregivers to use readily available tools to quickly access sophisticated analysis resources so that timely risk stratification and medical diagnosis can be implemented. As will be described below, the invention is applicable in a variety of other contexts to receive different input information and provide different results. For example, in one implementation, the invention enables anyone (medical provider or layperson), virtually anywhere, to take a short segment of video with their cell phone of, for example, an individual (subject) at the grocery store or other location with chest pain and immediately receive a diagnostic determination that the subject is having a heart attack, the subject's vital signs, and recommendations on the optimal course of action based on location and available resources. Meanwhile, the phone can automatically contact first responders with the information and relay location and contact information. In preferred implementations, the invention can employ video-based non-contact/minimal-contact predictive analytic (N/MCPA) capabilities to detect, determine, and provide medical diagnostic information by detecting and determining diagnostic indicators and patterns that are outside or below the threshold of human sensory or cognitive perception and/or are not ascertainable, in whole or part, in the same manner by currently available technologies. The invention may provide a non-contact diagnostic capability and/or it may function in conjunction with contact-non-invasive (CNI) and/or contact-invasive (CI) diagnostic procedures and interventions. Ultimately, it provides an augmented intelligence capability to enhance critical decision-making where, for these purposes, critical decision-making is defined as having some or all of the following four elements: 1) it is consequential, 2) it is time constrained, 3) it involves uncertainty, and 4) is made according to a framework that can be articulated, refuted, defended, and is capable of reaching different conclusions as underlying risk-variables, and thus risk-context, change.

This invention provides or enables diagnosis and risk-stratification with at least similar accuracy and timeliness to the standard-of-care for time-constrained and/or diagnostically challenging illness and injury while decreasing risks, and/or cost, and/or time associated with standard-of-care diagnostic paradigms by virtue of a non/minimal contact predictive analytic approach. Full realization of this technology provides an earlier-than-standard-of-care diagnostic certainty and/or risk-stratification threshold. This potentiates earlier intervention to mitigate or avert underlying medical risk and, in turn, potentiates decreased morbidity and mortality.

The system of the present invention may also provide recommendations for follow-on courses of action (COAs) to improve diagnostic accuracy and/or treatment and disposition measures. These recommendations may include repeat or continued monitoring with the capability or the acquisition of additional CNI data (electrocardiogram (EKG), telemetry, ultrasound/echocardiogram, touch screen motor function/coordination, wearable health/fitness devices, gyroscopic data from smartphone or other devices, etc.) or CI data (blood tests, biopsy, etc.) in order to improve diagnostic accuracy. Alternatively, this capability could be used in conjunction with these "contact" data inputs from initial patient evaluation. This technology will also provide non-contact vital signs in conjunction with or independent of providing diagnostic determinations. This technology may be utilized as an augmented intelligence capability, integrated into standard-of-care paradigms, or as a stand-alone capability. For recommendations on treatment or follow-on courses of action (COAs), this capability may also use location data, from devices such as smartphones, to provide optimal recommendations because, for example, the best available immediate COA for a patient with septic shock on a ship in the middle of the ocean without timely access to advanced medical care will likely be different than the best available immediate COA for a patient located one block from a major hospital.

For the purposes of this technology, "diagnosis" refers to the identification or nature of an underlying medical issue or illness based on a patient's recognized symptoms and/or based on physiologic and/or anatomic parameters that are not apparent to the patient or another individual without examination and/or testing. Diagnosis will be determined based on, but not limited to, statistical parameters such as sensitivity, specificity, and positive and negative predictive values. Depending on the medical condition under consideration, where the condition is in its pathologic and/or anatomic and/or physiologic progression, and/or the statistical parameters determined by the technology, the technology may function primarily as a "rule out" (sensitive) or "rule in" (specific) capability or both. For the purposes of this technology, "diagnosis" also refers to the processes of risk-stratification and triage whereby a patient or group of patients is determined to have a level of medical treatment and/or resource priority and/or need relative to other patients/individuals or relative to their individual presentation.

The system of the present invention may use standard commercially available cameras (such as webcams or those embedded in smartphones, body cameras (such as those used by law enforcement), Google Glass or other glasses-camera devices, and or GoPro® type cameras) and/or red-blue-green light specific cameras and/or infrared thermography cameras or adaptors to collect patient data including voice data. It may use camera devices mounted in static locations, carried and employed by human beings, or carried and employed on vehicles, planes, boats, submarines, or any form of conveyance or platform (human operated, remote control, or autonomous) to collect data. It may also use data from cameras or other devices that is not expressly collected for the purpose of use by this technology such as, but not limited to, television or security camera audio and video footage. Additional contact-based data may be utilized from initial evaluation or as required to further improve statistical characteristics of diagnoses. The data may be acquired by the patient, a bystander, medical provider, or through another source and may be (remote or local) user initiated, autonomous or semi-autonomous. Data will then be processed with techniques including, for example, motion microscopy (MM) and/or remote photoplethysmography (rPPG) and/or Computer Vision (CV) and/or Natural Language Processing (NLP) and will be analyzed with machine learning and artificial intelligence (AI) techniques to include, but not necessarily limited to, neural network (NN) techniques. For development of the predictive analytic models, acquired data will be compared with data acquired through standard-of-care treatment paradigms for the medical presentations of interest (Supervised/"Ground Truth" artificial intelligence (AI)/machine learning (ML) Model). Data inputs will also undergo Unsupervised learning to detect clusters and patterns in the input data that can be employed as a stand-alone diagnostic model(s) and/or in conjunction with the Supervised model(s) and/or can inform and drive data collection and inputs for development and employment of both supervised and unsupervised models. For employment of the predictive analytic model(s), the capability will not necessarily require the input of additional standard-of-care paradigm data. Of note, the input data does not have to be expressly captured for the purpose of the N/MCPA capability to be useful. For example, inputs from drones, security cameras and other input devices may be harvested for use in the system and may serve as the primary data input for the system in certain applications. Any relevant video/audio/other data could be analyzed by the capability to provide some level of diagnostic determination and information on physiologic and/or pathologic parameters on the video/audio/other subject(s) or to provide other desired outputs related to a subject and/or problem-set, including those of a non-medical nature. The data may be processed on the same device on which it is ingested, such as a smartphone, or may be transmitted to or uploaded on another device, network, or system for processing and analysis.

The invention thus addresses a number of objectives including:

1) Enhancing the efficiency and accuracy of diagnosis by experts.
2) Expanding and improving the diagnostic capability of non-experts.
3) Reducing the utilization, cost, and risk burden of contact and/or invasive diagnostic interventions.
4) Potentiating increased efficiencies in systemic resource utilization.
5) Allowing for rapid and/or simultaneous triage/risk-stratification and/or diagnostic evaluation of multiple patients with decreased risk to medical or other personnel conducting screening.
6) Expanding access to care including home or out-of-healthcare facility evaluation and monitoring and synergy with telemedicine.
7) Providing context specific recommendations for care and treatment where context is determined by absolute and relative medical risk/condition, location, resources, prevailing threats (weather, kinetic, etc.), etc.
8) Enhancing the risk, time, and cost efficiency of courses of care and treatment.
9) Allowing pathologic, physiologic, anatomic and other parameters to be captured through multiple sensor platform modalities (human with a sensor(s), drone with a sensor(s), static sensor(s), etc.) either expressly for the purpose of using this capability or for this capability to be applied to data captured for other purposes.

In accordance with one aspect of the present invention, a system and associated functionality are provided for use in medical evaluation of a TCCI condition of the subject. A user collects data regarding the TCCI condition using a user device, provides the user data to a processing system including a machine learning module, and receives output information from the processing system for use in treating the TCCI condition of the subject. The nature of the user device may vary depending on the context. For example, in the case of emergency treatment outside of a medical facility, the user device may include a smart phone operated by a first responder or layperson. In the context of treatment at a medical facility, the user device may be a smart phone or may include a laptop, tablet, or other data terminal. In any case, the user device may be used to acquire and transmit data from one or more sensors. The sensors may be provided as part of the user device and/or may be a separate sensor devices. For example, in the case of a smart phone, a video clip and or audio clip of the subject may be provided, or an evaluation of motor skills may be acquired by having the subject manipulate a touchscreen. In other cases, data from a separate sensor such as an infrared camera, a pulse oximetry sensor, medical equipment for obtaining vital sign information, or the like may be uploaded to the processing system using the user device.

As noted above, a variety of types of sensor information may be obtained including video information, infrared video information, audio information and others. This sensor information may be processed at the user device and/or at the processing system to obtain various types of data for processing by the machine learning module. This may include non-contact data, contact data, and standard of care or medical record data. For example, image information such as red-blue-green or infrared video information may be used to acquire information concerning temperature, skin color, blood perfusion, skin moisture, respiratory action, facial action, eye movement and blink rate, pupillary response, posture, movement, gait, joint function, motor coordination or other parameters as well as variability thereof. Audio information may be used to derive vocal biomarkers related to articulation, speech patterns, tone, rate, and variability thereof. The contact data may involve, for example, touchscreen and/or other fine motor inputs to evaluate fine motor coordination, gyroscopic data to monitor gait and other motor characteristics, and inputs from wearable health, wellness or medical monitoring devices. The standard of care data may include medical history and medical records, diagnostic studies, prior diagnoses, and information regarding disposition or outcome of prior treatments. It will be appreciated that many other types of data may be processed. Indeed, any medical or other information regarding the subject that can assist in risk analysis or developing treatment options may be ingested and processed by the system.

The processing system is operative for preprocessing the input data from the user device so that it is suitable for use in the machine learning module and then employing the machine learning module to generate output data concerning risk stratification and medical diagnosis. The machine learning module generally operates in two modes; a learning mode where models are developed for the various data environments and a processing mode for evaluating live data against the developed models. Machine learning is a well-known field that relates to computer-based tools that can learn from and make predictions concerning data without being explicitly programmed as to the details of the analysis. In this case, the input data from the user device, e.g., the sensor data or various parameters developed from the sensor data, can be used for risk stratification and developing treatment options. In this regard, much of the input data can be preprocessed to provide value and attribute sets, e.g., metadata identifying the data as temperature data, arterial oxygen saturation data, pulse rate data, etc. coupled with a value for that data element. The data can thus be readily characterized by a labeled feature space representation. Subspace models may be developed for subsets of the data. All of this lends itself to data modeling and development of sets of optimal training data that seed and support the machine learning process. This can result in supervised classification of this data that is often accurate and reliable. The subspace models may be developed with respect to various subspaces having reduced numbers of dimensions. Moreover, the data may be normalized to enable comparisons across different subjects. During real-time analysis, similar preprocessing may be applied with respect to the input data. The resulting preprocessed data can then be processed by the live processing branch of the machine learning module to identify correlations to the model data and generate corresponding outputs concerning risk stratification, medical diagnosis and/or treatment options (medical evaluation information). This output information can then be provided to the user via the user device.

As noted above, the invention thus encompasses a system and associated functionality. From the perspective of the user, the user employs a user device to provide, to a processing platform (e.g., the device itself and/or via a telephony/data network), input data including sensor data and receives medical evaluation information via the user device. From the perspective of the processing system, the processing system receives input information including sensor data, pre-processes the input information to obtain a dataset suitable for processing by a machine learning module, operates the machine learning module to generate medical evaluation information, and outputs the medical evaluation information to the user. The user device and/or processing system may further be operative for contacting first responders; forwarding medical information (e.g. including processed or unprocessed video information) to the first responders, accessing other sources of information such as medical records and statistical or demographic information, and applying various filters relating to privacy or user preferences regarding the information. In this manner, users including expert and nonexpert users can provide information regarding a condition of a subject and receive timely and accurate information regarding risk stratification, treatment options and other medical evaluation information.

In other implementations, as will be described in more detail below, input information such as sensor information may be obtained autonomously or semi-autonomously. In many important applications of the present invention, the ability of the user to explicitly interact with the system may be limited or a user's attention may be required elsewhere. For example, in battlefield environments or other emergency settings, it may be impractical for the user to activate sensors or respond to prompts on a touchscreen device. Accordingly, input information may be obtained from an autonomous source such as a drone or an available security camera or other device. Similarly, a user may simply leave a device such as a cell phone operating in audio or video mode to continuously acquire information that can be understood and analyzed by the system.

Relatedly, it will be appreciated that the information ingested by the system may be provided by any suitable source, then may be processed by the system, and output information may be provided to one or more system users different than and/or independent of the source of the input information. For example, the system may ingest information from drones, security cameras, and other sources that are not necessarily dedicated components of the system. Such information may be analyzed and alerts, reports, or other information may be provided to interested and authorized parties such as security personnel, medical personnel, first responders, or others.

As discussed in greater detail below, the invention is not limited to medical applications. Moreover, the time constraints are often dependent on context. Thus, for example, different time constraints apply to different medical conditions and different time constraints apply to other contexts such as an impending hurricane, a security threat, or the like. The system of the present invention is capable of understanding such time constraints, understanding trade-offs relating to timeliness and completeness of information for evaluation, as well as other factors affecting the analytical framework. Further use cases and associated analytical considerations will be understood from the description below.

BRIEF DESCRIPTION OF THE DRAWINGS

For a more complete understanding of the present invention, and further advantages thereof, reference is now made to the following detailed description taken in conjunction with the drawings, in which:

FIGS. 3A-3B show a schematic diagram illustrating operation of a processing system of a risk stratification and medical diagnosis system in accordance with the present invention for data collection, correlation and model training;

FIGS. 4A-4B show a schematic diagram illustrating operation of a processing system of a risk stratification medical diagnosis system in accordance with the present invention for model deployment.

DETAILED DESCRIPTION

In the following description, the invention as set forth in certain contexts relating to use by a non-expert, or layperson, in an emergency environment and use by experts (e.g., doctors and other medical care providers) in a medical facility. While these examples are useful in illustrating the flexibility of the invention, it will be appreciated that the invention is applicable in other contexts such as for use by first responders, use by combat medical personnel, use by staff medical personnel in schools, businesses, and other entities, and other environments involving nonexpert, semi-expert and expert users. Moreover, while the invention is described below for use in connection with certain examples of evaluating TCCI conditions, it will be appreciated that various aspects of the invention are more broadly applicable, including outside of medical contexts. Thus, the following description sets forth a number of examples relating to medical applications and then discusses a variety of other non-limiting use cases. Accordingly, the following description should be understood as illustrative and not by way of limitation.

Figure 1:
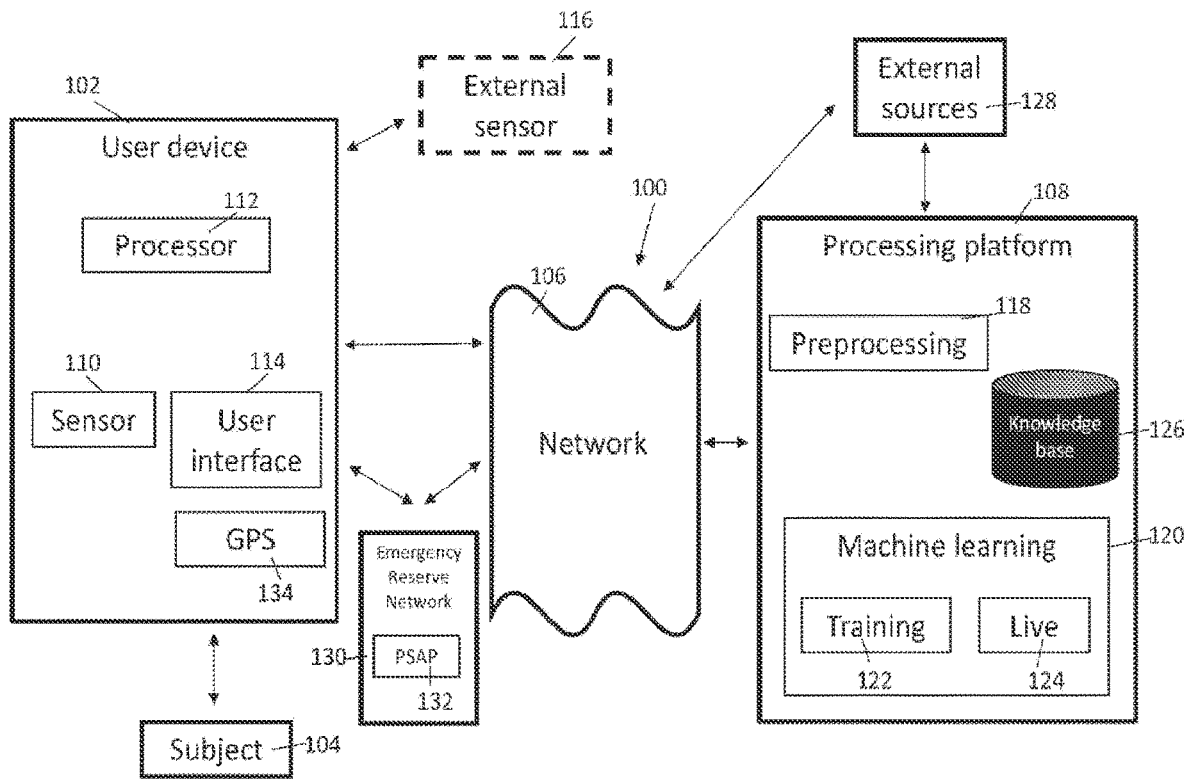
FIG. 1 is a schematic diagram of a risk stratification and medical diagnosis system in accordance with the present invention showing a first use case related to field use outside of a medical facility.

FIG. 1 is a schematic diagram of a Predictive Diagnostic Information Capability-Technology (PreDICT™) system 100 in accordance with the present invention. More specifically, FIG. 1 illustrates the system 100 in connection with a first use case relating to use of the system in a medical context and in the field, i.e., outside of a medical facility. Such use may be by a nonexpert users such as a layperson, by a first responder, or others. Moreover, data for the system 100 may be collected by medical providers, laypersons, users, subjects, or a third party not expressly for the purposes of the system. Data may be ingested and utilized for diagnosing and treating novel patients or it may be captured and compared against previously ingested data for a specific patient or group of patients. Previously ingested data may have been for the purposes of establishing a baseline or for the purposes of providing diagnosis and treatment or for another purpose altogether. However, for purposes of illustration, the illustrated system 100 generally includes a user device 102 for use by a user assisting a subject 104, a processing platform 108, and a network 106 for connecting the user device 102 to the processing platform 108. The system 100 may also involve an emergency response network 130 that includes public-safety answering points (PSAPs) 132 or similar network infrastructure in secure and unsecure, classified and unclassified military, maritime, disaster or other communication networks.

The illustrated user device 102 may include, for example, a smart phone, tablet computer or similar device. The user device 102 includes one or more sensors 110, a processor 112, and a user interface 114. As will be understood from the description below, a variety of types of sensors may be utilized including, for example, the device's video camera, the device's touchscreen, a microphone, or the like. Optionally, external sensors 116 such as an infrared camera, a pulse oximetry sensor, a digital thermometer or the like may be used in conjunction with the user device. For example, such sensors may be incorporated into a wearable in communication with the user device. Information from other types of sensors, such as impact monitors implemented in helmets for sports or military use, may also be employed.

In alternate use cases, such as battlefield environments or applications that ingest information from drones, available security cameras, or other sources, different workflows may be involved, for example, not involving an interactive interface for data acquisition. In the illustrated use case, the user interface 114 can be used to access the processing platform, to input information about the subject or the condition at issue, to provide information about the location or environment or other information that may be useful by the processing platform 108. The user interface may be implemented via voice activation, a touchscreen, a keyboard, graphical user interface elements and the like. The functionality of the sensor 110 and user interface 114 may be executed on the processor 112. The processor 112 is also operative for executing a variety of input and output functions, for example, related to interfacing with the processing platform 108.

The system 100 may also use information regarding the location of the user device 102. Where the user device 102 includes a GPS module 134 or other location information provisioned by satellite constellations, such information may be reported to the processing platform or used to route first responders to the user device 102. In other cases, location information may be provisioned by a cellular network technology such as angle of arrival, time delay of arrival, cell ID, cell sector, microcell, or other location technologies. Such location information may be provided to the processing platform 108 and emergency response network 130 via the user device 102 or via a separate pathway, e.g., from a network location information gateway. Location data may also be derived from recognition by the technology of environmental signatures including, but not limited to, image and acoustic signatures at a specific location that serve to localize, at some level of specificity, where the technology is being applied.

The system 100 may be implemented via a variety of architectures. For example, the functionality described in more detail below may be cloud-based such that little or no logic is required on the user device 10 to the implement the functionality. Alternatively, an application may reside on the user device 102 to support all or certain functionality of the system 100. For example, certain preprocessing may be executed locally to support the machine learning functionality of the processing platform 108. As a still further alternative, some of the logic may be implemented within the emergency response network 130, for example, at a PSAP 132. Thus, for example, a layperson assisting a subject 104 in an emergency environment may dial an emergency phone number (e.g., 911 in the United States) via a telephony or data network (e.g., VOIP). In such cases, the emergency call may be routed to an appropriate PSAP 132 via conventional network processes. Emerging technologies allow files to be uploaded from the user device 102 to the PSAP 132, including video and audio files. Accordingly, sensor information and other information from the user device 102 can be routed to the PSAP 132 which may in turn interface with the processing platform 108 to implement the functionality described herein. As will be understood from the description below, in many important use cases, such as battlefield environments or in the aftermath of a natural disaster, networks may not be available or may be limited. In such cases, the system may be implemented to function using local resources, satellite communications or emergency networks and the functionality may adapt to such environments.

The processing platform 108 processes the sensor information and other information from the user device 102, determines risk stratification information as well as medical diagnosis and treatment option information based on machine learning technology, and provides output information to the user device to assist the user in treating the subject 104. The illustrated processing platform 108 includes a preprocessing module 118, a machine learning module 120 and a knowledge base 126. The preprocessing module 118 performs a number of functions to prepare the input data from the user device 102 for use by the machine learning module 120. In this regard, the input data may need to be processed to obtain various subject parameters. For example, video data from the user device 102 may be processed to obtain information regarding temperature, perfusion, respiratory action or various motor functions, as described in more detail below. Audio information may be processed to determine certain vocal biomarkers such as speech patterns, tone or rate. In addition, the input data may be annotated and classified, regions of interest or signals of interest may be selected, the data may be normalized, and features may be extracted. Thus, a variety of metadata may be associated with the input data to support the machine learning functionality.

The machine learning module 120 includes a training mode 122 and a live mode 124. In the training mode, training information is provided for use in developing models that can be used to generate risk stratification and medical diagnosis information. In the live mode 124, live data from a user device 102 is processed using the developed models to generate output information to provide to the user device 102. Various supervised and unsupervised machine learning technologies may be employed as described in more detail below The knowledge base 126 stores information used by and generated by the pre-processing module 118 and the machine learning module 120. This may include training data, model information, statistical data, demographic data, medical record information, and any other information that is useful in developing and executing the machine learning models. One advantage of implementing the system 100 using a centralized processing platform 108 is that, over time, a rich knowledge base accumulated over many experiences concerning different kinds of conditions for different subjects will be available to improve the accuracy of evaluations. It will be appreciated that, although the processing platform 108 is shown as a single element for purposes of illustration, the functionality of the processing platform 108 may be distributed over many machines and may be geographically distributed to improve response. For implementations of this technology where processing is either desired or required on a localized and/or individual device or platform, the technology application is updated from the centralized processing platform.

The processing platform 108 may also access certain external sources 128. Such external sources 128 may be used to gather information to assist in developing and executing the models of the machine learning module 120. This may include medical record information from medical facilities and government sources, medical records for specific subjects 104 being evaluated, demographic information, e.g., from private and government sources, modeling tools, and other information. Such information may be provided directly to the processing platform 108 or may be accessed by a user device 102 or emergency response network 130. In connection with the user device 102, emergency response network 130, processing platform 108 and external sources 128, data may be filtered or otherwise processed (e.g., anonymized, aggregated, or generalized and through use of methods such as Federated Learning) to address privacy concerns. For example, the use of particular items of information may be controlled by the user or subject 104, by policies implemented in connection with the system 100, medical facilities, or other entities, or in accordance with applicable regulations.

Figure 2:
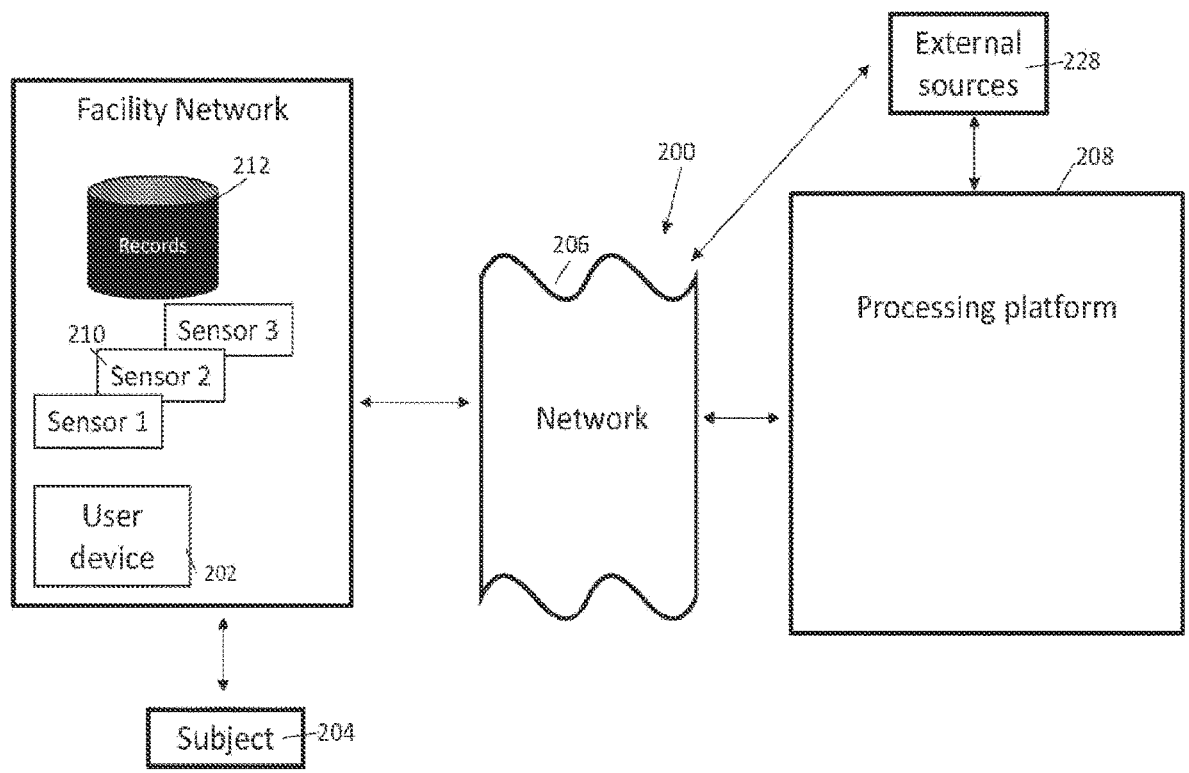
FIG. 2 is a schematic diagram of a risk stratification and medical diagnosis system in accordance with the present invention showing a second use case related to use within a medical facility.

FIG. 2 shows another use case of a PreDICT system 200 in accordance with the present invention. The illustrated system 200 includes a user device 202 for use by a user in treating a subject 204, a processing platform 208, external sources 228 and a network 206 for interconnecting these various elements. The network 206, processing platform 208, and external sources 228 are generally similar to the corresponding elements described in connection with FIG. 1 and such description will not be repeated.

In this case, however, the user device 202 is implemented in connection with a facility network 214. For example, the facility network 214 may be a local area network or other network associated with a hospital, clinic, or other medical facility. The user device 202 may connect to the facility network 214 to access patient records 212, upload sensor data from the user device 202 and/or other sensors 210, and access various other network-based resources. For example, the user device may comprise a tablet computer or intelligent medical device. In this regard, information from a variety of sensors 210 may be available for transmission to the processing platform 208. Thus, a patient and medical facility may have a variety of vital sign and other information that is continuously or periodically monitored by the sensors 210. An application executed at the user device 202 and/or processing platform 208 may harvest sets of data from the sensors 210 on a defined schedule or on demand. It will thus be appreciated that, in the illustrated use case, the processing platform 208 may have access to a rich data set for processing and may provide correspondingly accurate and detailed reports to the user device 202 for use by skilled and expert users.

Much of the immediately preceding discussion has focused on contexts where a user is actively involved in initiating actions or inputting information. In many emergency contexts that form an important application of the present invention, the user's ability to activate sensors and input information may be limited or the user's attention may be required for other purposes. Thus, it will be appreciated that the invention may operate differently in other contexts or use cases.

To understand the functionality of the PreDICT system and the manner in which users will interface with the device, it is important to understand one of the key use cases and certain attributes of this use case, which are applicable to multiple other use cases.

USE CASE: Employment by a battlefield medic during a kinetic engagement taking care of a close and personal friend who has been badly wounded. There are multiple considerations in this scenario as to how users optimally interact with the capability: 1) Physical considerations—the user's hands and/or gloves may be covered in blood, dirt and fluid. The medic may be copiously sweating, thus impairing or precluding interaction with the PreDICT device/interface. This may occur at night and the tactical situation may prohibit a bright touchscreen. Night vision compatible screens still encounter the problems with blood, dirt, sweat, etc. These factors make it very difficult to interact with a touchscreen or keyboard, 2) The user may be in a high emotional state and his cognitive and technical bandwidth may be consumed by taking care of the casualty, his friend. Every requirement to actively interface with the capability, other than to get exactly the information the medic needs, unnecessarily draws on his already limited bandwidth and requires more time in a time-constrained problem-set. As long as the sensors are active and appropriately oriented, the PreDICT system is acquiring, processing, analyzing, and outputting information with minimal requirements for user interface. The PreDICT system can communicate this information to him through multiple means such as a screen display and/or audio information through the medic's radio headset (such as a Peltor headset). If the PreDICT system detects that the user is not optimally caring for the patient and assesses that an intervention is not necessary or that another intervention or course of action is preferable, it can "escalate its communication" with the user through various auditory and/or visual and/or tactile prompts.

- If the PreDICT system requires more information to determine the desired outputs, the capability can prompt the user to enter or acquire more information. The user can then do this by adding or adjusting a sensor capability or by providing voice, touchscreen, or keyboard inputs.
- Employment of multiple technical capabilities in medical and other scenarios have encountered the two key issues described above: 1) Physical considerations make it difficult to interact with the device, and 2) The device places high demands on the bandwidth of the user that is otherwise required to resolve the problem at hand, which effectively makes the technical capability part of the problem. The PreDICT system will avoid these limitations and liabilities.
- The bottom line is that, during the period of employment, the PreDICT system will require minimal effort or input from the user.

The PreDICT system, as a sensor and/or device and/or system and/or network, can be activated ("turned on") actively, passively, directly, or remotely to include the ability of the PreDICT system to self-activate in response to certain signals or signal patterns. For example, it detects gunshots, 9-1-1 is dialed, or it detects a deceleration pattern indicative of a car crash. It can also go into specific modes based on these signals.

Once activated, the PreDICT system will extract, process, and analyze data from the subject and the environment to determine what mode it needs to be in and will function accordingly. It may have one or several default settings that it will activate in response to specific signals to place it in a specific mode. Or, it may prompt the user to place it in a specific mode if it cannot extract the necessary or sufficient information or if it does not have the computational bandwidth to extract, process, and analyze the information and determine the appropriate mode.

PreDICT system users will have the ability to select certain modes and/or menus via voice, touchscreen, keyboard, or other sensor inputs. Typically, a user would select these modes outside of or in anticipation of a specific scenario or rapidly via voice or other prompts as the scenario presents. These menus will range from broad to specific. For example, broad menus cover different use case domains such as "medical" and "intentionality." Within the "medical" heading there are multiple different chief complaints, body systems, anatomic regions, and/or subsets of pathology, etc. Within the "intentionality" heading there are multiple options such as "threat," "truthfulness," etc. If the user knows that they will encounter, or have a high probability of encountering, a trauma patient they may elect to place the capability in a "trauma mode." In another scenario, and for a different domain use case, the user may place the device in "threat mode" to determine if an individual in their environment represents a threat. The purpose for preselecting modes be to preserve computational bandwidth on a PreDICT device and/or network where the capability would otherwise need to extract, process, and analyze sensor data to determine that it was in a trauma or threat scenario.

In summary, the interface functionality of the PreDICT system ranges from a default with minimal to no user interface requirements during PreDICT application to, if desired and feasible, intensive interface between user and capability. The PreDICT user interface can also be a hybrid along a spectrum between minimal interface (system is only outputting information to user) to intensive manual interface by the user into the capability. The tradeoffs between these ends of the spectrum entail a balance between the bandwidth and physical capability of the user to interface with the capability and the computational bandwidth of the PreDICT capability.

As noted above, the machine learning processes implemented in connection with a training mode and a live data mode. This may alternatively be denoted as model training and model deployment. These processes are illustrated in FIGS. 3-4.

Figure 3B:
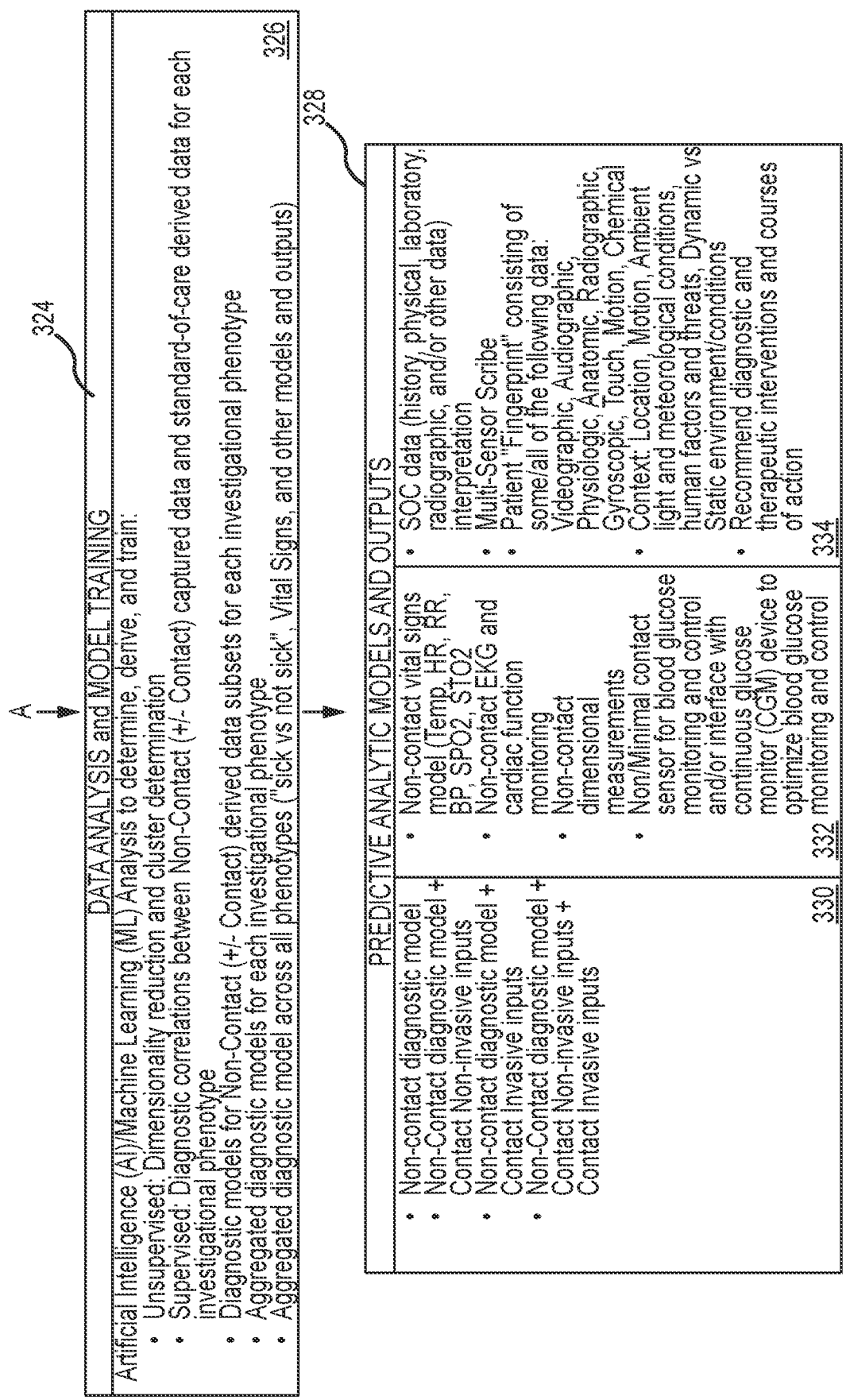

Referring first to FIG. 3, the model training process 300 generally includes data acquisition (302), data processing (318) or preprocessing, data analysis and model training (324), and development (328) of noncontact predictive analytic models. In the illustrated process 300, data acquisition (302) involves non-contact data acquisition (304), other data acquisition (306), and standard of care data acquisition (308). The non-contact data acquisition (304) and contact data acquisition (306) processes may be implemented by users in connection with live medical evaluations or by users entering training data. In the case of users involved in live medical evaluations, the data may be entered in response to prompts of a user interface or in response to questions from a PSAP operator or other person. For example, when a user accesses a processing platform of the PreDICT system, the user may be prompted to enter information regarding a current condition being evaluated, e.g., by selecting "chest pain" from a drop-down menu or otherwise describing a medical condition via a structured or free-form data entry. In response to such an input, the processing platform may execute branching logic and present additional user interface screens depending on the information entered by the user on previous screens. Such screens may prompt the user to obtain sensor information and upload the sensor information to the processing platform. For example, the user may be prompted to obtain a video clip of the subject's face and neck region and upload the video file together with an audio recording of the patient to the processing platform.

As shown, the noncontact data (304) may include video data (310) and audio data (312). The video data may be obtained using any type of camera device including but not limited to a standard webcam, a smart phone camera, Google Glass or other glasses-camera devices, GoPro® type cameras, body mounted cameras; static cameras such as security and surveillance type cameras; cameras mounted on mobile platforms such as aerial, ground based, or aquatic/maritime vehicles or autonomous or remotely operated vehicles; another red-blue-green camera; low light; and/or an infrared thermography video camera. Video data utilized by this technology may be obtained/extracted from video not expressly recorded for the purposes of applying this technology. Such cameras may be used to obtain a video recording of the head and neck region or other body areas of interests of the subject to acquire information indicative of any of the following or combinations, variability or other derivatives thereof: temperature; skin color, perfusion, or moisture; lesions, wounds, blood or other abnormalities; respiratory action; facial action unit; eye movements and blink rate; pupillometry, eye abnormalities—injection, discharge, etc.; posture, movement, gait, joint function, and motor coordination; anatomic abnormalities—amputations, deformities, swelling, wounds, etc.; treatments rendered— airway devices, vascular access, bandages, tourniquets, etc.; and extraction of audio/video to determine medications and/or other treatments provided. Such cameras may also be used to obtain information on the environment where a subject is located (or with the environment as the subject) such as location imagery; visual and light parameters; and dynamic motion signatures in the environment. The audio data, which may be obtained as an audio track accompanying a video recording and/or may be obtained separately through any capable recording device and/or derived through data processing techniques such as motion microscopy (MM), may include information indicative of vocal biomarkers for the subject and/or others in the environment related to articulation, speech patterns, tone, rate, and variability thereof. Audio data may also include specific words, phrases, and/or word phase patterns related to the subject and/or others in the environment. Audio data may also include acoustic patterns and/or signatures related to geolocation and/or the nature of the location, conditions, and scenario.

The other data (306) involves data that may be obtained via contact between the subject and a sensor and may include data on motor function or other parameters of the subject and/or environment (314). For example, the subject may be prompted to interact with materials or graphical objects presented on a touchscreen and/or to interact with other equipment to evaluate fine motor coordination and variability thereof over time. Additionally or alternatively, sensors such as gyroscope based instruments may be applied to the subject or embedded in devices carried by or on the subject for other purposes such as smart phones or wearable fitness devices to obtain gyroscopic data for monitoring gait and other motor characteristics.

Accelerometer/impact monitors may be incorporated in sports or military helmets or otherwise incorporated on a person, means of conveyance, or other location and used to obtain impact data. As a still further alternative, wearable health/wellness/medical monitoring devices may be employed to obtain various kinds of sensor information such as pulse oximetry data, heart rate and heart rate variability data, respiration rate, and parameters related to the autonomic nervous system. Such data acquisition may further involve chemical and/or biologic and/or nuclear radiation sensors (contact and/or non-contact) to detect end tidal CO2 (ETCO2), ketones, acetone, alcohol metabolites, or other chemicals/toxins, biologic material or organisms, or radiation emitted from the human body via respiration, perspiration or other means and/or to detect chemicals/toxins, biologic materials or organisms, or radiation in the environment. Electronic stethoscope, doppler, and ultrasound data may be obtained to capture cardiac, pulmonary, and/or other auditory, motion, and internal structure data related to the subject. Further data on the subject may be captured using continuous glucose monitoring (CGM) devices and/or from implanted cardiac defibrillators and pacemakers. Data may also be obtained on the environment, location, and the nature of the location and environment to include ambient temperature and moisture data; global positioning system (GPS) and or cell phone tower triangulation data; and dynamic motion signatures from GPS and gyroscopic devices to determine motion parameters in multiple dimensions for scenarios such as, but not limited to, travel on ground, maritime, or aerial platforms. Lastly, data acquisition may include "expert games." Expert games are a mechanism to build or augment data sets for training machine learning and/or artificial intelligence systems and for those systems to build models. Expert games use real or hypothetical case studies of problems in domains of interest to build "games" for relevant experts. Through the "playing" of these games, key information about expert decision making and the problem-sets posed by the "games" can be extracted to create data sets for machine learning and/or artificial intelligence analysis, learning, and modeling. The PreDICT system will use expert games to augment training and functionality for application to multiple domain scenarios. Expert games will particularly apply when training and modeling high-consequence, low frequency events.

Sensor platforms may include fixed camera and/or audio recording or other devices for the purpose of obtaining input data related to the diagnostic and/or predictive capabilities of this capability or fixed sensors not explicitly for the purposes of this capability, such as surveillance cameras. Sensor platforms may also include human or vehicle (to include ground, air, and maritime platforms both manned, unmanned, and autonomous) mounted or transported sensors. Remotely piloted and/or autonomous ground, air, and maritime vehicles will provide important platforms for PreDICT as sensor platforms and/or as network nodes for PreDICT capability and/or by using PreDICT capability as the decision-making application to guide the functionality of the platform as in the case of autonomous systems.

The standard of care (SOC) data (308) may be obtained from the subject, the user, patient records of the subject, patient records from a medical facility, peer-reviewed literature, government databases, other third-party databases, and other sources. Examples (316) of such data include records of the subject's medical history and physical exam data such as history of present illness/injury (HPI) data, past medical and surgical (PM/S Hx) to include allergies and medications, physical exam findings and vital signs, possibly including electronic stethoscope data. In addition, the data may be obtained from diagnostic studies such as electrocardiogram (EKG) and telemetry, laboratory studies (blood, urine, cerebral spinal fluid (CSF), etc.), Radiology studies (e.g., x-ray, computed tomography (CT), ultrasound (U/S), and magnetic resonance imaging (MRI)), coronary patency evaluation (e.g., treadmill stress test, coronary CT, and percutaneous coronary intervention (PCI) studies), cardiac catheterization, surgical findings, pathology and autopsy findings, electroencephalogram (EEG), and standardized screening and clinical decision tools and models. The standard of care data (308) may further include diagnoses such as those made at emergency department (ED), clinic or point-of-care disposition, in-hospital diagnoses and diagnoses made at hospital discharge (if admitted). Finally, the data (308) may include disposition/outcome data from the point-of-care (ED vs. home vs. other), from the ED (home vs. admit—floor, step down, ICU, etc.), and/or from the hospital (home vs. SNF vs. rehab). The disposition/outcome information may also include status information such as whether the subject is still hospitalized and their current status or whether the subject is deceased. Standard of care data and other medical data may also be acquired from other treatment environments and paradigms (e.g. non-clinic, non-emergency department, non-hospital based under some standard conditions) such as deployed military medical treatment facilities, humanitarian medical programs, medical disaster response scenarios, austere medical events or programs, and/or emergency medical services The data processing (318) involves pre-processing of input data so that it is suitable for use in a machine learning process. As noted above, this may involve processing raw inputs to obtain the desired parameters. For example, infrared camera data may be processed to obtain temperature information and variations thereof or video files may be analyzed to obtain information regarding facial or eye movements. Such input information or parameter information may be further supplemented to assist in processing by the machine learning module. For example, noncontact data (304) and/or contact data (306) may be processed (320) to annotate and classify the data, to select regions of interest and signals of interest for further processing, to perform individual component analysis for example with or without motion microscopy and/or remote photoplethysmography and/or computer vision, and/or natural language processing, to normalize the data to facilitate comparisons, and to perform feature extraction. The standard of care data (308) may be processed to annotate and classify the data, to normalize the data, and to perform feature extraction among other things.

The data analysis and model training (324) involves processing the training data to develop models for use in analyzing live data. In the illustrated process 300 this involves using artificial intelligence/machine learning analysis to determine, derive, and train (326) the models. Artificial intelligence techniques may include, but are not limited to, neural network techniques. A variety of machine learning processes may be used in this regard including unsupervised machine learning for dimensionality reduction and cluster determination; supervised machine learning to develop diagnostic correlations between noncontact and/or contact capture data and standard of care derived data for each investigational phenotype; developing diagnostic models for noncontact and/or contact derived data subsets for each investigational phenotype; developing aggregated diagnostic models for each investigational phenotype; and developing aggregated diagnostic models across all phenotypes (sick vs. non-sick and vital signs) among other processes.

The results of the data analysis and model training (324) is the development of noncontact predictive analytic models (328). These include diagnostic models (330), noncontact models (332), and other outputs (334). The diagnostic models (330) may further include standalone non-contact diagnostic models, non-contact diagnostic models plus contact non-invasive inputs, non-contact diagnostic models plus contact invasive inputs, non-contact diagnostic models plus contact noninvasive inputs plus contact invasive inputs. The noncontact models (332) may include non-contact vital signs models, including temperature, heart rate (HR), respiratory rate (RR), blood pressure (BP), pulse oximetry (SPO2), tissue oxygen saturation (STO2); non-contact electrocardiogram (EKG)(or functional EKG equivalent) and cardiac function monitoring; non-contact dimensional measurements (e.g., video and/or sonographically derived measurements to determine the size and volume of anatomic, pathologic, or other human and non-human/non-living structures or entities); and a non/minimal contact sensor for blood glucose monitoring and control and/or interface with a continuous glucose monitoring (CGM) device to optimize blood glucose monitoring and control. The other outputs (334) may include standard of care (SOC) data (history, physical, laboratory, radiographic, and/or other data) interpretation; a "Multi-Sensor Scribe" that converts data streams into written, graphic, or other documentation formats for direct integration into existing electronic medical records (EMR) systems or other purposes; a "fingerprint" of a subject or environment including some or all of video, audio, pathologic, physiologic, anatomic, radiographic, gyroscopic, touch, motion, and chemical data; contextual models of the environment to guide decision making that include location, motion, ambient light and meteorological conditions, human factors and threats, and assessment of whether the context is static versus dynamic; and recommendations on diagnostic and therapeutic courses of action.

FIG. 4 illustrates a PreDICT model deployment process 400. In particular, the process 400 is illustrated with respect to four diagnostic models and additional models developed by the machine learning training process. The illustrated process 400 is initiated by data acquisition (402). In this case, the data acquisition (402) generally corresponds to the noncontact data acquisition (404) and contact data acquisition (406) described above in connection with FIG. 3. Indeed, it is anticipated that live data will also be processed through the model training process to further develop the models. Thus, the noncontact data (404) may include video data (408) and audio data (410), and the contact data (406) may include motor inputs and standard of care contact-noninvasive (CNI) and contact-invasive (CI) inputs (412) as described above. In addition, the illustrated data processing (414) may include various preprocessing functions (416) as described above in connection with FIG. 3.

However, in this case, the data analysis (418) involves deploying the trained machine learning models (420) with respect to individual or aggregated data streams and phenotypes to determine diagnostic probabilities, vital signs, and other outputs. Specifically, in the case of deploying the non-contact/minimal-contact predictive analytic models (422) with respect to live data involves deploying a non-contact/minimal-contact diagnostic model (424), deploying another non-contact model (426), and/or providing other outputs (428). The potential outputs of the diagnostic model (424) may include diagnostic and therapeutic outputs. The diagnostic output may be expressed with statistical confidence and/or representations thereof with respect to: 1) the presence or absence of illness or injury; 2) the presence or absence of a specific illness or injury; 3) a probability distribution for particular diagnoses; and any of items 1-3 with recommendations for follow-on action to improve diagnostic statistics and accuracy. Such follow-on actions may include repeat or continued non-contact predictive analytic (NCPA) monitoring and/or acquisition of noninvasive contact data (touchscreen, EKG/telemetry, ultrasound/echocardiogram, etc.) and/or acquisition of invasive contact data (laboratory tests, biopsy, etc.).

For the therapeutic output, the described diagnostic capability can be linked with existing medical reference databases or texts and/or can utilize machine learning and/or artificial intelligence, such as neural network capabilities, to determine the most appropriate therapeutic courses of action once a diagnosis is made and recommend this course of action to the user based on their level of expertise and current context. In this regard, the therapeutic output may take into account whether the user is a patient at home, a physician stopped at the scene of a traffic accident, a physician in an emergency department, etc.

The other models and outputs (426) may include a non-contact vital signs model (temp, HR, RR, BP, SPO2, STO2), a non-contact EKG and cardiac function monitoring model, a non-contact dimensional measurements model, and a non/minimal contact sensor for blood glucose monitoring and control and/or interface with a continuous glucose monitoring (CGM) device to optimize blood glucose monitoring and control. The other outputs (428) May include standard of care (SOC) data (history, physical, laboratory, radiographic, and/or other data) interpretation; a multi-sensor scribe that converts data streams into written, graphic, or other documentation formats for direct integration into existing electronic medical records (EMR) systems or other purposes; a "fingerprint" of a subject or environment including some or all of video, audio, pathologic, physiologic, anatomic, radiographic, gyroscopic, touch, motion, and chemical data; a contextual model of the environment that includes location, motion, ambient light and meteorological conditions, human factors, threats, and a measure of static versus dynamic conditions, and other parameters to guide contextual decision making on treatments and courses of action; and recommendations on diagnostic and therapeutic courses of action The present invention is this applicable with respect to a variety of conditions and in a variety of contexts as set forth below.

Examples of Medical Conditions and Contextual Circumstances where technology provides utility: (Note: "Utility" refers to any of "ruling in", "ruling out", decreasing time to diagnosis, decreasing required interventions to arrive at diagnosis, decreasing cost, monitoring for deterioration/improvement, etc.)

Conditions: Including but not limited to:
  Neurologic:
    Stroke (Cerebrovascular Accident (CVA)) and/or Transient Ischemic Attack (TIA)
    Traumatic Brain Injury (TBI)
    Spinal cord injury, compression, ischemia, infection
    Altered mental status
    Dementia vs. Delirium
  Psychiatric/Mental Health/Developmental Conditions:
    Suicidality or risk for self-harm
    Homicidality or risk of harm to others
    Depression
    Mania
    Delirium
    Post Traumatic Stress Disorder (PTSD)
    Autism
  Cardiopulmonary/Chest Pain:
    Heart Attack (Acute coronary syndromes (ACS))
    Dys-/arrhythmia
    Aortic Dissection
    Pulmonary Embolism (PE)
    Pneumothorax (PTX)
    Esophageal Rupture
    Pneumonia
    Asthma/COPD
    Congestive Heart Failure (CHF)
  Cardiovascular:
    Blood pressure monitoring
    Hypertensive urgency/emergency
  Pre-/Shock States:
    Distributive
    Hypovolemic
    Cardiogenic
    Obstructive
    Dissociative
    Resuscitation monitoring
  Infectious Disease:
    Systemic infectious processes (i.e. Sepsis, COVID-19, etc.)
    Localized infectious processes (i.e. Necrotizing fasciitis, cellulitis, pyelonephritis, etc.)
  Intraabdominal and OB/GYN Processes:
    Appendicitis, Cholecystitis, Diverticulitis, Abdominal aortic aneurysm (AAA), etc.
    Ectopic pregnancy
    Ovarian torsion or cyst rupture
  Ischemic Processes (not already mentioned):
    Embolic processes resulting in ischemic limb or other organ/region
    Testicular torsion
  Musculoskeletal:
    Joint injury such as sprain, dislocation, or meniscus or labral tear
    Bone fracture
  Trauma:
    Blunt
    Penetrating
    Burn
  Toxicology:
    Toxidromes
    Intoxication
  Metabolic and Endocrine disorders (e.g. Diabetes, glucose monitoring)
  Malignancies/Cancer Contextual Circumstances:
  Conventional medical settings: Doctor's office, Emergency Department, In hospital
  Mass casualty events/incidents (aka. MASCAL, MCI)—Triage, risk-stratification, diagnosis
  Austere and/or resource constrained environments
  Pre-hospital (EMS)
  Out of hospital (laypersons)
  Telemedicine
  Disease surveillance
  Time challenged diagnoses (e.g., TBI)
  Out of hospital monitoring
  Military applications and combat settings
Outputs:
  The PreDICT system not only recommends what intervention a patient requires but also the logistics and sequencing of that intervention by processing not only information about the patient but also information about the risk-context surrounding the patient and their illness/injury. Several examples are below.
  Example 1—The PreDICT system determines that a trauma patient requires endotracheal intubation because of an increasing inability to protect his airway. However, the PreDICT system also determines that the patient is hypotensive and has a probable pneumothorax. The PreDICT system determines that positive pressure ventilation from endotracheal intubation will cause immediate decompensation by: 1) increasing intrathoracic pressure in the setting of hypotension, which will decrease blood return to the heart via the vena cava, decrease cardiac preload, and decrease cardiac output and 2) it will convert the pneumothorax to a tension pneumothorax from the positive pressure ventilation, further increasing intrathoracic pressure and accelerating decompensation. Following this analysis PreDICT recommends an intervention sequence of: Step 1) Simultaneous chest tube placement and rapid infusion of 1 unit of whole blood, Step 2) Endotracheal intubation once Step 1 complete and blood pressure achieves a minimum of XYZ/xyz.
  Example 2—The PreDICT system determines that a patient at Hospital A with chest pain is experiencing an ST elevation myocardial infarction (STEMI) and requires a cardiac catheterization to relieve the coronary artery obstruction. Hospital A does not have this capability but Hospital B does. This is a time-constrained medical problem-set ("time is myocardium") and the patient's probability of survival and optimal future cardiac function is inversely related to the time to the procedure. The patient can be transported by helicopter or ground ambulance. The ambulance can have the patient loaded and depart in 10 minutes. It will take 5 minutes to get the patient to the cardiac catheterization lab at Hospital B once the patient arrives. The helicopter can have the patient loaded and depart in 30 minutes. It will take 10 minutes to get the patient to the cardiac catheterization lab at Hospital B once the patient arrives. The PreDICT system can evaluate historical transport data and real-time air and ground traffic data to determine that transport by helicopter will place the patient in the cardiac catheterization lab at Hospital B twelve minutes faster than transport by ground ambulance at this time of day due to heavy traffic volumes. Alternatively, the PreDICT system may recommend that the patient should be administered thrombolytic treatment for the STEMI at Hospital A because the transport time to Hospital B by either mode is prohibitively long given the patient's STEMI and the time since onset. (Thrombolytics are a "second line" treatment for STEMI if the patient cannot undergo cardiac catheterization within a recommended time window.)
Use Cases, Dual/Alternative Use Cases and Potential Applications:
NOTE: These dual uses are not necessarily endorsed by the inventor.
  Example of PreDICT employment towards a medical problem-set on a military special operations direct action raid.
    Consider the problem-set of a seriously wounded Soldier in the middle of a firefight during a raid to capture an enemy combatant who is barricaded in a building that is defended by a capable opposing military force. The successful resolution of this problem-set requires averting the determinative risk associated with the casualty's injuries. For this to happen, the casualty must receive immediate mitigating treatment for his injuries by the assault force medic (AF) medic and a casualty evacuation (CASEVAC) helicopter must get the patient to a surgical team to avert the determinative risk associated with the injuries. This sequence of events requires multiple decisions by multiple decision makers. For optimal medical care to occur in the risk-context, the ground force commander (GFC) must make decisions about the ongoing operation—continue the tactical initiative and complete the objective then focus on the casualty or break contact now and focus on the casualty? The GFC's decision will be affected by the status of the casualty in relation to multiple other risks, including the risks of failing to accomplish the objective, in the risk-context. The GFC's decision will, in turn, affect the CASEVAC pilots' decision making—should they launch to the objective now and loiter in the air near the objective awaiting a call to land and pick up the casualty or should they stay on the ground at their current location until a decision is made by the GFC? If they launch now it will shorten the time it takes the patient to get to surgery but may constrain them if they don't have enough fuel to air loiter for a sufficient period and ultimately extend the time to surgery. Decisions by each/any of the medic, GFC, and pilots will all affect the others' decision making. These individual and collective decisions will, in turn, affect the decision making of the receiving surgical team. An optimal outcome to this problem-set requires a shared mental model of the problem-set by each of the decision makers and the ability for each decision maker to have the information they require to make their respective decisions. The PreDICT system provides the capability for each decision maker in this (and analogous) problem-sets to understand the problem-set in real time to gain a shared mental model and the capability to selectively feed each decision maker with the information and recommendations most critical to their respective decision making sphere. This capability also saves time and cognitive and technical bandwidth by automatically communicating information that otherwise or traditionally needs to be shared via deliberate action, such as through a radio call or typing into a device. Users can determine what decision makers will have access to the capability and, in turn, shared mental model and/or information and recommendations. Furthermore, in this or similar medical examples (or in other examples where documentation is critical), the PreDICT system can generate a medical record of injuries, vital signs, treatments, etc. extracted from video, voice, and other sensor inputs that can be viewed in multiple formats, printed to hardcopy, sent electronically, and/or uploaded to a medical records system to follow the patient through their course of care all the way back to the United States. In the scenario above, the PreDICT system could be employed on/by/through multiple platforms, or combinations of platforms, such as personnel carried smartphone type devices and/or on overhead manned or unmanned aerial platforms with relevant sensors.

Population Health Surveillance:

COVID-19 has revealed the challenges of conducting widespread population health surveillance to include accurately identifying those at risk for the disease and those at risk for decompensation who have the disease.

For COVID-19 and similar current or future health problem-sets, the PreDICT system provides a capability for widespread, non-/minimal contact population health surveillance to identify at risk or infected patients, to include capabilities for contact tracing, and a capability to predict patient outcomes and/or assist with determining the prognosis of patients who have the disease of interest.

The non-/minimal contact capability also provides a significant measure of safety to medical and non-medical personnel who would otherwise be required to come into close contact with patients/persons at risk of spreading the pathogen.

In addition to decreasing medical risk and direct associated medical costs, it also provides cost benefit in multiple other ways. For example, the non-/minimal contact vital signs capability decreases contact between medical personnel and infected or potentially patients which, in turn, decreases personal protective equipment (PPE) requirements and associated costs. Because the PreDICT system can rapidly assess multiple patients to perform triage and/or diagnosis, it can decrease "bottlenecks" at triage and enhance the efficiency of emergency departments. This allows the patients with the highest medical needs, including those who do not have COVID-19 (or a similar pathogen), to receive needed care in a timelier manner. By creating these efficiencies in triage, the PreDICT system can also free up healthcare personnel otherwise dedicated to perform triage to perform other critical medical tasks.

Benefits to managing a pandemic: "Social distancing", "Lockdowns" and other "restrictions" have been implemented as means to control the spread, and subsequent related morbidity and mortality, of COVID-19. These measures each have social, economic, political, and other tradeoffs. The PreDICT system provides a mechanism to rapidly determine an individual's risk of having the infection through physiologic screening, location data, and other data inputs and/or the ability to specifically diagnosis infection through additional sensor inputs. Furthermore, this mechanism could be widely distributed and employed through platforms such as smartphones, existing video surveillance networks, sensor equipped kiosks, and/or other data collection platforms. This empowers individuals, schools, businesses, etc. to conduct screening at the individual, family, acquaintance, pupil, patron, employee, etc. level and, in turn, use privacy controls to aggregate data for (near) real-time population disease surveillance. A higher level of "diagnostic certainty" regarding the state of COVID-19, or similar pathogen, allows decision makers to apply more targeted use of control measures such as "lockdowns" and, consequently, lowers the economic, social, political, and other risks associated with these measures.

Furthermore, the PreDICT system can utilize other data sources and inputs to determine the risks and tradeoffs of infection control measures (such as "lockdowns") relative to the risk of COVID-19 death and disability and make recommendations to decision makers regarding the risk-benefit of these infection control measures, to include secondary effects such as the probability of increased death and disability due to depression and suicide, child abuse, etc.

Medical Intelligence:

Determine health status of individual(s) based on (any) video/audio data:

Casualties or potential casualties at an incident site (such as from drone footage)

Adversaries, enemies, competitors, etc.

Hostages, POWs, etc.

Human Intentionality: By measuring physiologic parameters, voice, motion, etc., this invention could determine or elucidate human intentionality or truthfulness in multiple circumstances Negotiations or gambling Interrogation: This capability could be used to support "tactical questioning" in military operations and/or could be used to augment or replace existing polygraph techniques.

Determine "suspicious" activity or intent, either through real-time monitoring (such as through an airport or sensitive site video surveillance system) or at a later time by applying the PreDICT capability to previously captured video, audio, or other data.

(Potentially) Hostile confrontations such as those encountered by law enforcement or military (i.e. Does this person have hostile intent? Is this person a combatant? Is this person about to shoot me?) to de-escalate, escalate, and/or improve target discrimination By extension, this capability could be used in autonomous or semi-autonomous weapons systems An example to illustrate some of the capability described above would be the use of PreDICT technology in a weapon optic that assisted the user of the weapon to rapidly and accurately discriminate hostile from non-hostile and legitimate from non-legitimate targets. Consider the case of a SWAT Team or military element clearing a complex structure, such as a multi-story, multi-room building, containing multiple combatants and non-combatants. The rules of engagement (ROE) may stipulate that lethal force is authorized against any military age male (MAM) demonstrating hostile intent. Hostile intent may be obvious such as if an individual is pointing a weapon at you. However, it may also include certain actions and postures (termed "presentations") that are generally understood to mean that an individual is reaching for a weapon, about to initiate an explosive device such as a suicide vest, or about to undertake some other high-threat defensive or offensive action. The individuals clearing the building must make decisions about the use of lethal force in a decision space that is often less than a second. First, they must determine if an individual is a MAM. Secondly, they must determine if the MAM demonstrates hostile intent. The consequences of misjudging a potential target could mean that either a non-legitimate target is engaged and killed or that a member of the SWAT/military element is engaged and killed because they did not accurately identify the target and/or their decision-action cycle was outpaced by the enemy's decision-action cycle. It is also important to understand that clearing a structure (Close Quarters Battle (CQB)) is highly stressful and, consequently, higher order decision making functions are suboptimal, which further challenges target discrimination. Factors such as low light, high noise levels, lack of familiarity with local norms of male and female dress may make it difficult to distinguish between men, women, and children. Once a MAM is identified, it will take some period of time to determine if that individual is demonstrating hostile intent. An adversary's hostile presentation must be fairly far along for a human being to perceive it. By the time the hostile intent is recognized it may be too late to react before the adversary can initiate their own hostile action. PreDICT capability could be embedded as part of a weapon's optic system to rapidly identify legitimate and hostile targets and either alert the individual employing the weapon or, under certain parameters, automatically discharge the weapons against the threat. Alternatively, the PreDICT system could be employed apart from the weapons system but with the same practical functionality. PreDICT could also be employed as a decision-making capability for autonomous or semi-autonomous weapons systems. The fundamental concept is that by identifying patterns and indicators that are below or outside of human sensory and/or cognitive capabilities, PreDICT can markedly improve both the speed and accuracy of the decision-action cycle leading to enhanced target discrimination and, if warranted, neutralization.

Human and Environment Identification/Discrimination: The PreDICT capability could be used to identify individuals or discriminate between individuals based on movement/motion characteristics (video and/or gyroscopic), and/or Audio characteristics, and/or physiologic profile characteristics and/or other data inputs to derive a unique "fingerprint" for individuals or subgroups of individuals, such as to identify those with risk characteristics for certain disease states, as a security mechanism for accessing computer systems, etc. These data streams could also be applied to environments and/or scenarios to derive environmental and/or scenario specific "fingerprints" and signatures.

Medical Monitoring: The PreDICT system can be used for the longitudinal monitoring of chronic medical conditions to 1) improve treatment and maintenance of the condition, 2) individualize treatment and maintenance of the condition, and 3) anticipate and/or diagnose when a chronic medical condition transitions to a TCCI. Representative examples include cardiac monitoring and glucose monitoring for diabetics.

Cardiac Monitoring: Non/Minimal contact continuous or periodic monitoring to ascertain cardiac rate, rhythm, and/or cardiac output to identify potential or actual cardiac emergencies and/or recommend individually targeted medication, dietary, activity, and lifestyle modifications to optimize cardiac function.

Glucose Monitoring: Non/Minimal contact continuous or periodic monitoring to ascertain blood glucose levels for diabetes and other conditions. This capability may be integrated with existing continuous glucose monitoring (CGM) systems such as utilizing existing CGM sensors, transmitters, and receivers or it may function through a different mechanism using data streams and processing techniques otherwise described for the PreDICT system. This capability can identify potential or actual hypoglycemic or hyperglycemic emergencies and/or recommend individually targeted medication, dietary, activity, and lifestyle modifications to optimize blood glucose levels.

Medical/Situational Monitoring: Used as a safety and/or early warning feature in multiple settings such as—

Baby monitors or other patient monitors to look for indicators of distress

Lock-out device for vehicles if driver is intoxicated, sleep deprived, or otherwise impaired Automatically slow and break a vehicle or switch an aircraft to autopilot if the operator becomes impaired or incapacitated Autopilot takeover when mental bandwidth is overloaded relative to the task or the environment. For example, when a pilot is performing the dangerous task of landing a jet aircraft on an aircraft carrier at night, their mental bandwidth is dedicated to the task at the possible expense of missing other threats in their environment, including the possible threat that they will not safely perform the landing. The PreDICT system can utilize sensors to monitor both physiologic parameters of the pilot (reflective of cognitive state) and threats in the environment (to include high-risk failure of the intended task) and initiate autopilot or other safety controls. This scenario is used as just one illustration. There are multiple domains where this type of safety control could be employed.

Human Performance Evaluation, Discrimination, and Training: ThePreDICT capability could be used to evaluate human performance across different domains, discriminate actual performance or performance potential between individuals or groups of individuals, and as a tool to improve to performance of individuals or groups of individuals through training feedback. For example, the National Football League (NFL) runs the annual NFL scouting combine ("the combine") to determine potential NFL prospects. During this event, participants undergo mental and physical tests to determine their potential for success in the NFL. The PreDICT capability could collect and use data from NFL prospects attending the combine (including their performance in the combine and other metrics apart from the combine) and performance data on prospects who make it to the NFL to derive predictive models to determine both success in the combine and success in the NFL. The PreDICT capability could then be applied to prospects prior to or apart from the combine to determine the potential for success in the NFL. This capability would have broad application across domains assessing human performance potential and suitability to include, but not limited to, sports, military, law enforcement, intelligence, aviation, music, etc. Furthermore, it would provide an additional mechanism for discriminating between candidates when multiple candidates are assessing for limited positions. By extension, the PreDICT capability could be used to identify physical, behavioral, or other performance characteristics requiring improvement towards a specific goal. Thus, the capability can be used as a training adjunct for performance improvement. By extension, this capability could also be used to evaluate, discriminate between, and improve the performance of teams or groups of individuals across different domains.

Drone Use Cases:
  As described elsewhere in this document, a key conceptual underpinning of the PreDICT system is to optimize the response to time constrained problem-sets by 1) increasing the speed and/or accuracy of diagnosis and/or 2) the efficiency of the intervention to resolve the problem-set, by mitigating or averting the underlying risk and/or 3) minimizing the risk associated with diagnostic and/or therapeutic interventions. This concept applies to both medical and non-medical problem-sets.
  Drones, which may include autonomous and/or remotely piloted aerial, ground, or maritime vehicles or devices, enable each of the factors enumerated above.
  The PreDICT system will be integrated with drones for multiple use cases where the drone will serve as a sensor platform and/or intervention platform and where PreDICT will serve as a capability to augment human or autonomous applications of the drone or will serve as the primary decision-making architecture for the drone.

Augmented Human Critical Decision Making Across Multiple Domains:
  Critical decision making, time-constrained expected value optimal stopping problems, and risk-context have been described as part of understanding PreDICT capability. These concepts and models are inherent to both the concept and functional capability of the PreDICT system as the system collects, processes, and analyzes manifestations of these concepts and models in the real world.
  Multiple domains in the human-physical world manifest and require critical decision making in a model similar to that described as time-constrained expected value optimal stopping problems nested in a risk-context to present a problem-set.
  We have primarily focused on decisions in the domain of medicine and human physiology and/or physical states. However, other examples include (but are not limited to): financial, political, social, military, and other domains as well as decisions bridging many domains. The PreDICT system can be applied to problem-sets in any of these domains.
  Below is a use case of the PreDICT system being applied in a non-medical, non-human physiologic domain.
  Consider the case of a hurricane in the mid-Atlantic Ocean heading towards the east coast of the United States from the perspective of the mayor of Charleston, South Carolina as a decision maker. Somewhere in the possibility-set is the scenario where that hurricane makes landfall directly at Charleston as a category 5 storm. In the event that this contingency materializes the mayor wants to ensure that the city has been completely evacuated and appropriately secured prior to the hurricane's arrival. But, also in the possibility-set is the scenario where the hurricane has no effect on Charleston at all. Evacuating the city is a costly decision but not evacuating is also a (potentially more) costly decision. Here, cost can be measured in multiple ways—human health and safety, economic, political, social, etc. All of these costs are risk-variables in the decision and help shape the risk-context and, in turn, the problem-set facing the mayor.
  Another consideration is that evacuating and securing the city will take time. If the mayor desires (or requires) a high level of diagnostic certainty regarding where the hurricane will make landfall and its strength when it makes landfall then, by that point, it may be too late to evacuate the city. It is likely that the mayor will have to accept an intermediate or low degree of diagnostic certainty to make a decision.
  Furthermore, the lens through which the mayor considers and processes objective information is influenced by emotion and biases. For example, the mayor will likely view the decision differently a month after Hurricane Katrina than 20 years after hurricane Katrina (assuming that similarly cataclysmic hurricane events don't occur in the interim).
  The PreDICT capability provides an augmented intelligence capability to assist decision makers with this type of decision, which fits the model of a time-constrained, expected value, optimal stopping problem with a determinative risk (the hurricane) in a risk-context resulting in a problem-set.
  In this and similar problem-sets, the PreDICT system can employ sensors to understand and advise the decision maker on their own physiologic state and, in turn, their emotional state and decision-making capacity.
  It can also ingest and employ multiple data sets, such as contemporaneous hurricane models, historical data on hurricanes and hurricane responses, traffic data and transportation data relevant to evacuating the city, and data derived from "expert games," etc. to model contingencies and make recommendations to decision makers.

Much of the discussion above has focused on particular applications of the invention in relation to certain emergency environments. However, as previously noted, the invention has broader applicability. This section describes and elaborates on fundamental aspects of the PreDICT system which, in turn, demonstrate how it might be applied across multiple and diverse use cases.

Key Points
  This section presents a model of Time-Constrained, Expected Value, Optimal Stopping Problems. This model demonstrates a type of problem for which the PreDICT system has utility as an augmented intelligence capability. It also demonstrates a conceptual model of PreDICT functionality and one mechanism by which the PreDICT system "thinks" about these problems as a machine learning and artificial intelligence application.
  The PreDICT system enhances the resolution of both time-constrained and non-time-constrained problem-sets in essentially the same manner, by using multiple sensor and data inputs to determine diagnostic patterns and indicators that are below or outside human sensory and cognitive thresholds. It then evaluates the underlying risk and the risk-context to recommend optimal interventions and the logistics and sequencing of those intervention. The fact that it does all of this at machine speeds, markedly faster than humans are capable of, is where it provides benefit for time-constrained problem-sets. It provides decision makers with a more accurate picture of the problem-set more quickly and recommends (or implements) the most time and risk efficient solutions.

The discussion elaborates on and defines the idea of "time-constraint."

The discussion examines different functional relationships regarding the PreDICT system as a device embedded capability versus a network/cloud enabled capability versus a hybrid.

Critical Decision Making (CDM)

Among its attributes and capabilities, the PreDICT system is a constellation of processes, methodologies, devices, systems and technologies to improve and/or augment and/or replace human critical decision making (CDM). Critical decision making is defined as having some or all of the following characteristics: 1) It is consequential by some objective or subjective definition, 2) It is time constrained by some absolute or relative criteria, 3) The decision(s) are made with some degree of uncertainty as to specifics of the underlying and enveloping problem-set (the determinative risk and/or risk-context) and as to the outcome of the problem-set with or without interventions to change the course of the problem-set (mitigate or avert the underlying determinative risk), and 4) The decision is made according to a framework that can be articulated, refuted, defended, and that is capable of reaching different conclusions as underlying risk-variables (and risk-context) change. Such a framework can also be viewed as the framework that defines the problem-set under consideration. Critical decision making is generally applied to time-constrained problem-sets. Risk, for the purposes of this discussion, is defined as the probability of an undesirable outcome—"consequential." Risk can manifest in multiple forms—harm, loss, uncertainty, etc.

This section examines a conceptual graphical and quantitative model of time-constrained problem-sets, examines how PreDICT capability can enhance outcomes for such problem-sets, examines the concept of "risk-context" and how the PreDICT system can enhance contextual CDM, and examines the concept of "time-constrained" as it applies to time constrained problem-sets.

Time-Constrained Problem-Sets as
"Time-Constrained, Expected Value, Optimal
Stopping Problems"

The Basic Construct of Time-Constrained Problem-Sets: Equations 1 and 2

Figure 5A:
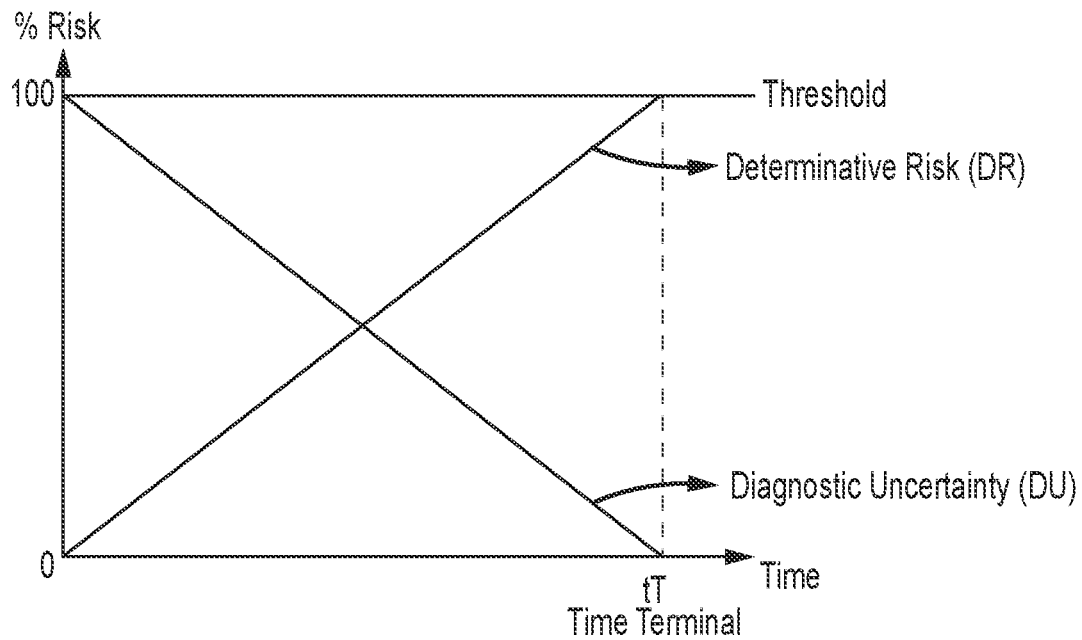
FIGS. 5A-11 are graphs depicting various time-risk relationships in various contexts and associated advantages of the present invention.

CDM and time-constrained problem-sets have a fundamental underlying characteristic: the underlying risk (the "determinative risk" (DR)) increases with time while the level of diagnostic uncertainty about the existence, nature, scope, specifics, etc. of the underlying risk decrease with time (see FIG. 5A) Thus, the underlying risk increases with time while the risk of diagnostic uncertainty decreases with time. We can also take the mathematical complement (1-risk) of the determinative risk and the risk of diagnostic uncertainty and say that potential benefit, or the ability to realize benefit in light of the underlying problem, decreases with time while the benefit of diagnostic certainty regarding the underlying problem increases with time (see FIG. 5B). The complement of DR (1-DR) is potential benefit (PB). The complement of DU (1-DU) is diagnostic certainty (DC).

The determinative risk (DR) is the underlying risk that effectively precipitates or defines a problem-set. It is typically non-self-limiting, meaning that it will not resolve in a favorable outcome without intervention to mitigate or avert it. Of note, it may not be the risk or the outcome that a decision maker is primarily concerned with within a problem-set but, nonetheless, it is the risk that significantly defines and/or circumscribes the problem-set. Most commonly, the DR does this by setting a time-constraint and, thereby, creates a problem-set where one may not have otherwise existed or places a new or additional constraint on an existing problem-set. Another way DR creates or contributes to a problem-set is by creating uncertainty or adding to uncertainty. Furthermore, a DR can define a problem-set without actually existing or being present. In order to affect or define a problem-set, the DR, from the perspective or assessment of a decision maker, must exist in a possibility-set and rise to some level of probability. So, even if another, and less consequential risk, is actually present the DR will define the problem-set until such time as the decision maker reaches a threshold of diagnostic certainty and determines the DR does not reach a sufficient level of probability for continued consideration. For understanding the conceptual model below, we will primarily consider the case where the DR does exist and a decision maker is focused on the DR.

In the case of DR establishing a time-constraint, the DR will increase with time or at some point in time until the DR exceeds some threshold within the problem-set and a (usually negative) outcome is realized. The time that this occurs is the time terminal (tT). The time terminal sets the time-constraint for the problem-set and, once it is reached, there is no possibility of realizing a beneficial or different outcome in the problem-set. Importantly, while DR may circumscribe a time constraint it is not always apparent to critical decision makers precisely what the time constraint is or that it exists at all. Time terminal (tT) is also the only point in the problem-set at which diagnostic uncertainty (DU) can be zero or, stated as a complement, diagnostic certainty (1−DU) can be 100%. (see FIGS. 5A and 5B)

Figure 5B:
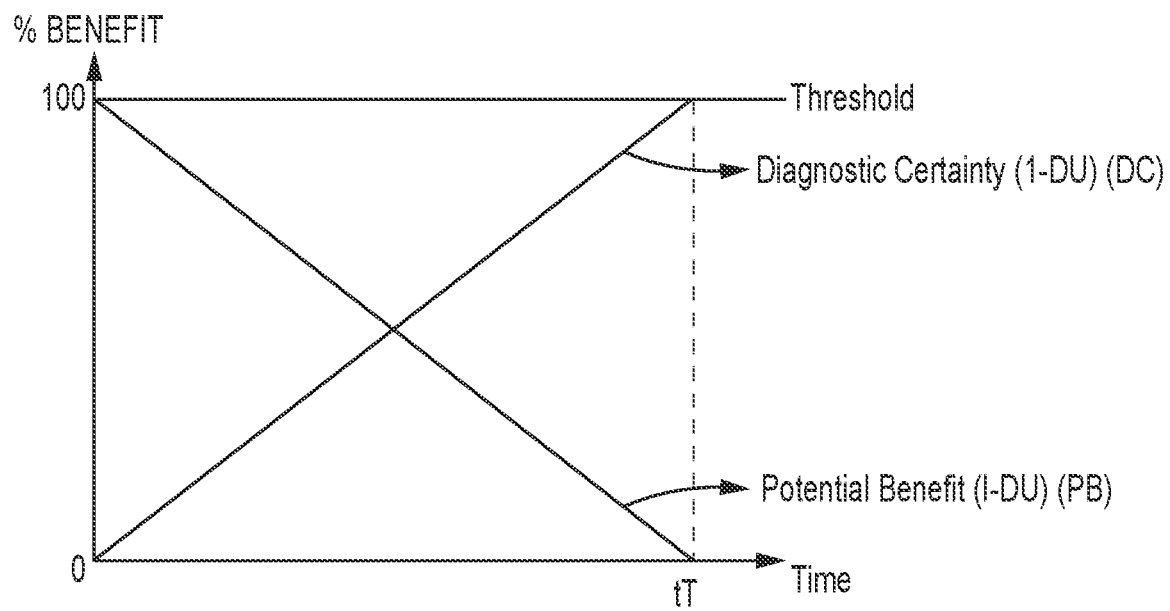

Critical decision-making is fundamentally about finding the optimal, ideally maximum, benefit value within the problem-set depicted in FIG. 5B. The mathematical relationship between increasing diagnostic certainty (DC) and decreasing potential benefit (PB) is defined by the function:

$$RB(t) = DC(t) \times PB(t) \qquad \text{Equation 1:}$$

Where RB is relative benefit. "Benefit" because in CDM we generally seek at least a beneficial solution (though we prefer optimal) and "relative" because benefit is not absolute and what constitutes benefit is in part relative to the alternative outcomes and the interventional risk applied and/or taken to achieve that benefit. Optimizing equation 1 will yield the highest possible RB for this representative problem-set.

Figure 5C:
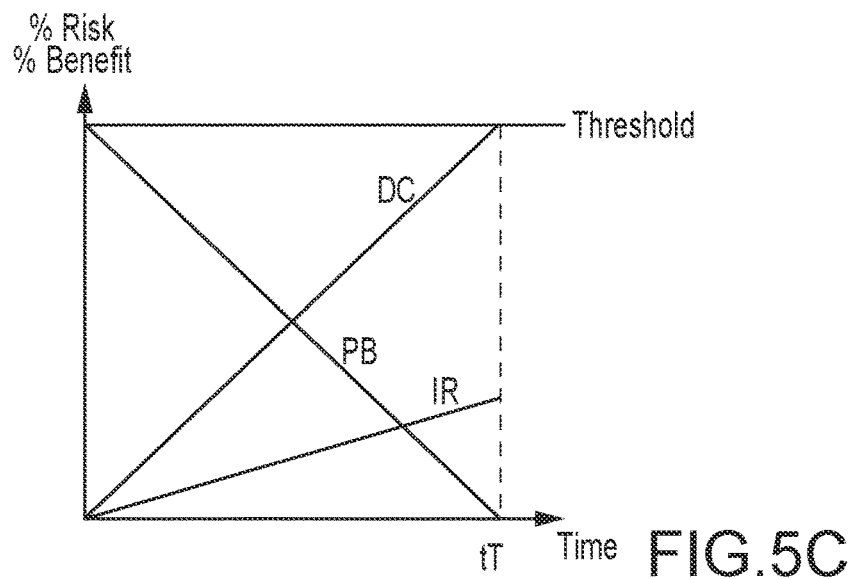

There is, however, another key risk-variable in determining RB; interventional risk (IR). To realize RB in a problem-set will require interventions to either increase certainty (diagnostic interventions) and/or to mitigate or avert the determinative risk (therapeutic interventions). These interventions will carry some degree of risk in some form. In the case of a time-constrained medical problem-set both diagnostic and therapeutic intervention will frequently carry risk in the form of direct risk of morbidity or mortality, either in the present or future. In addition, interventions, particularly diagnostic interventions, will carry risk in the form of time. It takes time to perform diagnostic intervention and it takes time to gain results from a diagnostic intervention. This elapsed time comes at the cost of increasing determinative risk (DR) or, stated differently, decreasing potential benefit (PB), while the diagnostic intervention is performed and resulted. A final consideration is that interventional risk often increases with time. Two reasons for this are: 1) because, as the determinative risk increases with time, a greater degree of intervention or a higher risk intervention is required to mitigate or avert the underlying risk and achieve relative benefit (see FIG. 5C), and 2) as time elapses in problem-set without the determinative risk being mitigated or averted, the "risk-density" of the problem-set increases—there is less time to achieve diagnostic certainty and/or optimally intervene. This increases the likelihood of applying an in extremis intervention—an intervention that is suboptimal (higher inherent risk and/or less likely to successfully mitigate or avert the determinative risk).

Accounting for IR, the problem-set is now defined by the function:

$$RB(t) = [DC(t) \times PB(t)] - IR(t) \quad \text{Equation 2:}$$

Note, this is essentially an expected value equation as a function of time. Solving a time-constrained problem-set (a time-constrained, expected value, optimal stopping problem) can thus be viewed as trying to optimize expected value by determining the specific point in time with the optimal balance of potential benefit, diagnostic certainty, and interventional risk required to mitigate or avert the determinative risk within a bounded period of time. The requirement for a decision maker to find "the specific point in time," and the inability to go back in time, create an optimal stopping problem. Furthermore, as the prevailing risk-context changes, it may alter the specific point in time at which the PB, DC, and IR risk-variables are optimally balanced to maximize RB. A function of the PreDICT system is solving problem-sets of the general model presented above. The PreDICT system accomplishes this by acquiring, processing, and analyzing more and different data than human beings are capable of, at machine speeds, in order to find diagnostic indicators and patterns that are below or outside the threshold of human sensory and cognitive capabilities. The PreDICT system uses this information to determine the most risk and time efficient intervention for the DR in the prevailing risk-context. Additionally, the PreDICT system will be able to derive a higher level of diagnostic certainty through non- and minimally-invasive techniques, which will serve to decrease the diagnostic interventional risk (IR) required at a given point in time to attain a given level of diagnostic certainty.

Determinative Risk (Potential Benefit) Curves

Figure 6A:
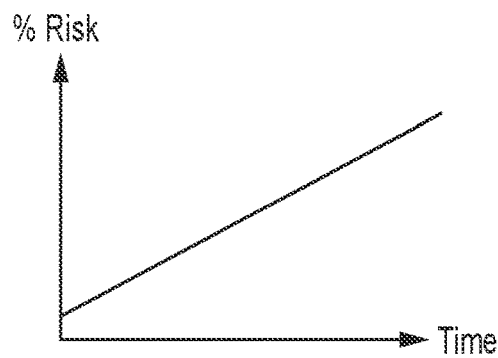
Figure 6C:
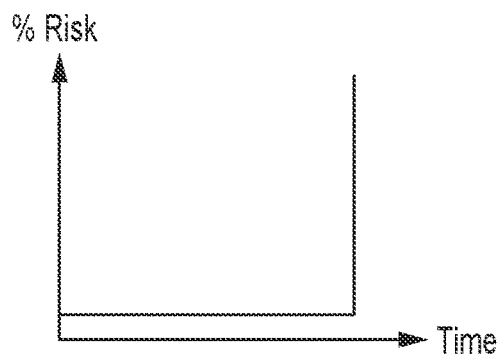
Figure 6B:
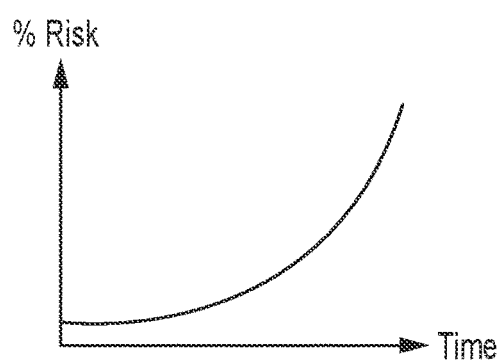

The initial challenge of CDM is recognizing that there is a critical situation and thus critical decision to be made. The model presented above demonstrates one, of perhaps many, pathways in a possibility and probability-set (problem-sets within a possibility and probability-set). For example, just because a patient has a penetrating chest wound does not mean they have a time-constrained critical injury. They may only have a superficial wound. However, the presence of the chest wound constrains the possibility-set; it places the presence of a life-threatening or other serious injury well within the realm of possibility. Other factors, indicators, and interventions will elucidate the actual probability. This constraining of the possibility set then presents the patient and, in turn, the critical decision makers charged with his or her care, with a set of determinative risk (DR) curves, each one representing the probabilities of various terminal outcomes (loss of life, chronic disability, etc.) as a function of time. Critical decision makers may (consciously or unconsciously) choose to focus on one or multiple of the DR curves, either in parallel or in serial. Levels of diagnostic certainty regarding any one DR curve may inform the level of diagnostic certainty regarding other DR curves in the problem-set. Furthermore, DR curves may take different forms all for different possibilities within the same problem-set. FIGS. 6A-6C demonstrate several representative DR curves, though these figures are by no means representative of all possible DR curves. Each type of curve has different challenges and complexities from the standpoint of solving a time-constrained, expected value, optimal stopping problem. This is important because it illustrates the complexity of the types of problems the PreDICT system has utility in solving and optimizing. For any possibility-set, there are multiple branches with different levels of probability that are often in dynamic interplay. The Hick-Hyman Law (also known as Hick's Law) describes an increase in the time required for a human to make a decision as the number of options in a decision set increase, essentially as the degrees of freedom and, in turn, the complexity of the decision increase. The PreDICT system will utilize more and different data than human beings and perform powerful processing and analytics at machine speeds which will potentiate better optimization of such complex problem-sets as measured by both the accuracy of solutions and the timeliness of the solutions.

A characteristic shared by each of the DR curves is that risk and/or risk-density increases with time. Essentially, for the problem-sets we are discussing, risk equals time and vice versa. Another way to state this is that, in each case, the probability of realizing the terminal outcome is generally more likely to occur at some time (t+x) than it is at time t, where (t+x)>t and t and x are positive numbers. The concept of risk increasing with time is relatively straightforward. The concept of risk-density is more involved. We will consider two examples to examine these concepts and reference the corresponding figures.

In example 1, consider a gunshot wound (GSW) to the abdomen that results in internal hemorrhage that over time progresses to hemorrhagic shock, increasing physiologic dysfunction, and, ultimately, death (the terminal risk in this example). The DR curve in this example generally corresponds to FIG. 6B. The underlying risk is progressing with time and the probability of realizing the terminal outcome (death) if appropriate intervention (to mitigate or avert the underlying risk, hemorrhage) is taken at time t is less than if appropriate intervention is taken at time (t+x), when the patient is experiencing more physiologic dysfunction. Stated differently, the patient has a higher probability of benefit (surviving) if intervention is accomplished at time t than at time (t+x).

In example 2, consider a single engine aircraft that experiences an engine malfunction at 30,000 ft above ground level (AGL). The aircraft is on a glidepath toward the earth and a fatal impact, the terminal outcome. The DR curve in this example generally corresponds to FIG. 6C. The time until impact is t30 at 30,000 ft and t5 and 5000 ft. t30>t5. The engine failure is not fundamentally worse at 5000 ft than it is at 30,000 ft. If the engine can be successfully restarted the probability of a positive outcome (avoiding a fatal impact and successfully landing the aircraft back at the airport) is the same. However, the risk-density of time is much greater at 5000 ft than at 30,000 ft. Some amount of time is required to 1) recognize that there is a problem, 2) diagnosis the problem, 3) determine what action to take, 4) successfully intervene on the problem, and 5) for that intervention to have the desired effect. Collectively, the time required for all of these to elapse/be accomplished is the "time of operational risk" (tOR). Theoretically, tOR is the same at 30,000 ft as it is at 5000 ft. However, because $t30>t5$ the risk density of time is greater at 5000 ft than it is at 30,000 ft; $(tOR/t5)>(tOR/t30)$. Basically, what this means is that, for time constrained problem-sets, as time elapses there is less time to identify and diagnose the problem, determine the appropriate intervention, perform that intervention, and for the intervention to take effect. If the time remaining until the terminal outcome is less than the time of operational risk then the terminal outcome is effectively unavoidable even if it has not yet been realized. Using this example, if $tOR>/=t5$ then, at 5000 ft, the engine cannot be restarted in a sufficiently short period of time to avoid fatal impact. Note, this same concept of the "risk density of time" and tOR also applies to the GSW in example 1. The PredDICT system decreases the time of operational risk (tOR) and decreases the risk of interventions (IR) required to diagnose and, potentially, to solve the problem.

Mitigating and Averting Determinative Risk

Figure 7A:
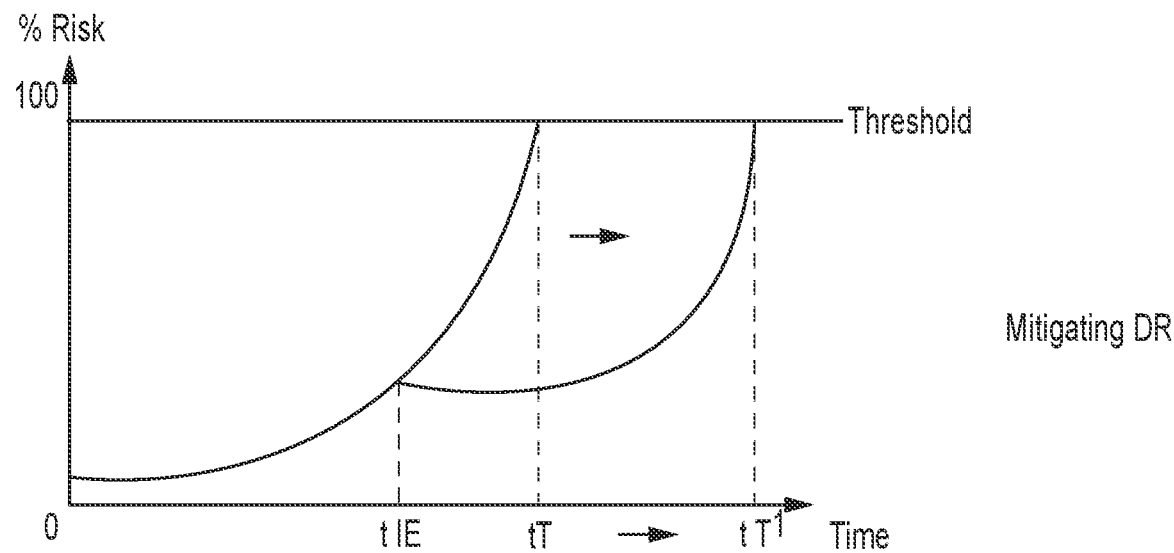
Figure 7B:
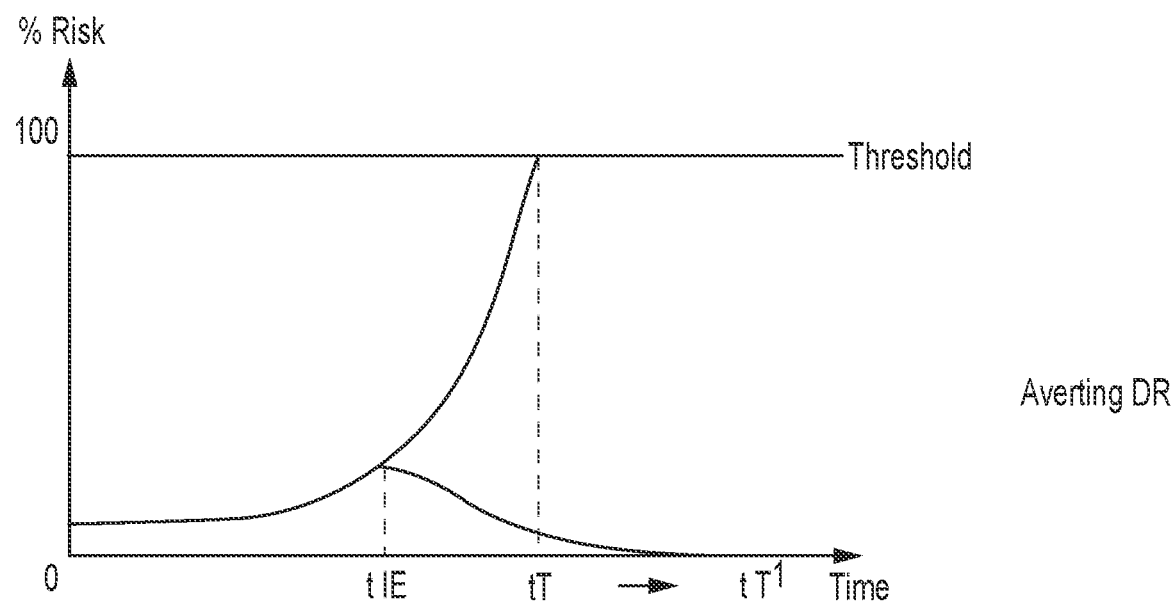

The sections above discussed "solving" time-constrained problem-sets (time-constrained, expected value, optimal stopping problems). What does it mean to solve them? What does a solution look like? Solutions to these problems entail mitigating and/or averting the determinative risk. Mitigating DR results when the DR, and resultant terminal outcome and time terminal (tT), is pushed further into the future. This establishes a new DR curve and a new time terminal (tT') (see FIG. 7A). It can be thought of as "temporizing the problem" (or transitioning one problem into another, ideally, lower risk problem) and allowing more time for critical decision makers to maximize diagnostic certainty, determine optimal interventions, and apply those interventions and for the interventions to take effect to either further mitigate the problem-set or to avert it completely. Stated differently, it allows for a longer tOR and/or it decreases the risk-density of time. Averting DR results when, through intervention, the subject of the DR (patient, system, issue, etc.) are "off-loaded" from the DR curve to a new curve that returns them to their original, or a new, baseline risk curve that is not time constrained and establishes a time of resolution (tR) (See FIG. 7B) FIGS. 7A-7B show representative examples of mitigating and averting risk using the DR curve from FIG. 6B. Time of intervention efficacy is denoted "tIE." Frequently, time-constrained problem-sets are approached by first applying a mitigating intervention ("buying time"), such as with a tourniquet to temporize extremity hemorrhage, followed by a definitive intervention to avert the determinative risk, such as a vascular surgery procedure to repair the injured blood vessel. The definitive intervention(s) "offloads" the patient from the new DR curve that results from the mitigating intervention and returns risk to some new or original baseline.

Operational Risk: Equations 3, 4, and 5

Figure 8:
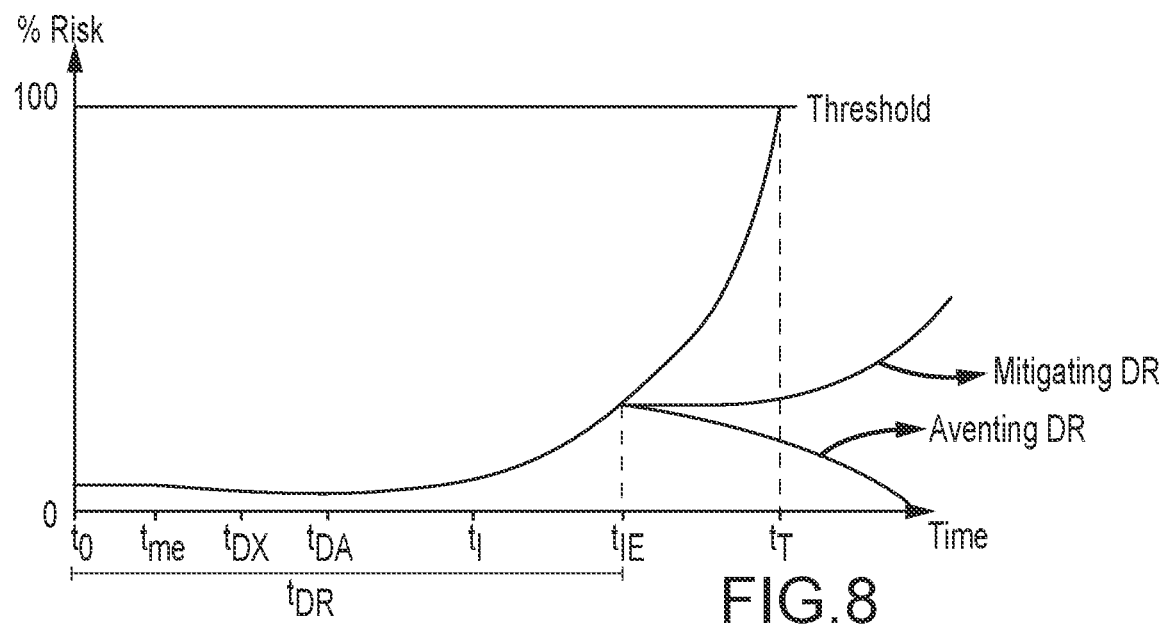

Operational risk (OR) is the time required, form the onset of a determinative risk (t0), to effectively mitigate or avert a determinative risk (DR). Operational risk (and the time of operational risk (tOR)) is comprised of multiple components and actions (see FIG. 8): 1) recognition that there is a potential or existing determinative risk (DR) and a problem-set, 2) diagnosis of the determinative risk (DR), 3) decision to act, what intervention to perform, and how to perform it, 4) performing the action/intervention, and 5) time for the intervention to reach efficacy. These components and actions are defined as follows:

1. Recognition that there is a potential or existing DR and problem-set: Time to meaningful contact (tMC). This is the point at which a critical decision maker is in contact with or engaged by a DR or problem-set to at least recognize that they exist and to form initial impressions as to the source, nature, and scope of the problem. Note, the tMC may, and frequently will, occur after some relative delay from the onset of the DR and problem-set.

2. Diagnosis of the DR: Time to diagnosis (tDx). The culmination of this period is the point at which a critical decision maker has reached a sufficient diagnostic threshold (has a sufficient understanding of the DR and/or problem-set) to consider moving forward with an action or intervention. Time to diagnosis is the period during which a critical decision maker is gaining certainty about the underlying determinative risk (DR). Note, an intervention might be a deliberate act of "doing something" (commission) or a deliberate act of "not doing something" (omission). Also, the action and/or intervention following from achieving a diagnostic certainty threshold may be intended to mitigate or avert the DR (ie. Therapeutic intervention) or to achieve a higher level of diagnostic certainty (ie. Diagnostic intervention). If it is a diagnostic intervention, the time to perform and result that intervention will extend the time of tDx.

3. Decision to act, what intervention to perform, and how to perform it: Time to decision to act (tDA). tDx is the period during which a decision maker gains certainty about the underlying determinative risk. tDA is the period during which they decide what action and/or intervention to take and the logistics and sequencing of that action/intervention for the determinative risk in the existing risk-context. Ideally, a diagnostic certainty threshold should (near) immediately precipitate a decision to act and action. However, there are multiple reasons why this might not occur, such as the baseline or contextual expertise of decision makers is such that they do not initially recognize that a diagnostic certainty threshold has been reached, a lack of knowledge or skills to take action, or personal attributes such as individual "risk tolerance." At any rate, some period is required following attaining a threshold of diagnostic certainty and the formulation of a plan of action and the implementation of that action. It is important to stress that tDA is not simply a decision regarding what action/intervention to take. It also a decision about how to take that action/intervention—Who should perform it? When? Where? What sequencing and logistics are required to optimize the intervention and potentiate success? The answer to these questions depends on the risk-context and the ability of the decision maker to optimally answer these questions depends on their operational expertise in the risk-context. We will discuss this more later.

4. Performing the intervention: Time to intervention (tI). This is the time to complete an intervention. For example, giving a patient a unit of blood is an intervention that begins when the critical decision maker (ie. Doctor, nurse, medic, etc.) determines that giving a unit of blood is the action to initiate. It ends when the last drop of that blood flows into the patient. All of the actions and decisions involved in the process in between—type and screen, getting the blood to the patient, starting an IV, hanging the blood, etc.—are part of that intervention and the time to intervention (tI).

5. Time for the intervention to reach efficacy: Time to intervention efficacy (tIE). This is the period from the completion of the intervention until the intervention achieves the desired effect of mitigating or averting DR. For example, a unit of whole blood given to mitigate hemorrhagic shock is not immediately effective. It must restore blood volume, oxygen carrying capacity, and blood clotting components. This, in turn, restores perfusion to tissues and protects against further blood loss. This allows lactate and other toxic metabolites to be removed from the body and for pH to normalize. At this point, after whatever period of time was required for the above effects to transpire, the patient's physiologic dysfunction has been improved and the DR mitigated.

Time of operational risk (tOR) is defined by the following equation:

$$tOR = tMC + tDx + tDA + tI + tIE \quad \text{Equation 3:}$$

Identifying and understanding these components and the breakdown of tOR is critical as we develop our understanding of relative benefit (RB) as a function of time. Equations 1 and 2 do not account for the time distributed nature of decision making, action, and results, which is a reality of time-constrained problem-sets and significantly challenges decision makers. Accounting for this yields a time function of the general form:

$$RB(tFUTURE) = [(DC(tNOW) \times PB(tFUTURE)] - IR(tNOW) \quad \text{Equation 4:}$$

Considering tOR and its components yields the more specific function:

$$RB(tOR) = [DC(tDA) \times PB(tOR)] - IR(tI) \quad \text{Equation 5:}$$

Time of operational risk (tOR) components, or some of the components, will often be in dynamic interplay. For example, there may be several loops between tDX and tDA before a clear intervention and/or pathway to performing that intervention is identified. The components of tOR can be conceived of as a more comprehensive and detailed OODA (Observe, Orient, Decide, Act) Loop process that is not complete until the "act" is resulted. Furthermore, the components may not be executed stepwise in a linear fashion. There may be overlap and all or some components and sub-components may be occurring in parallel. For example, for a time-constrained medical problem-set, such as a critically injured trauma patient, diagnostic certainty will be ascertained, at least through clinical observation and feedback, throughout the entirety of the patient-physician encounter even after tDX has been accomplished. What ultimately matters is the tOR, the time at which the DR is successfully mitigated or averted. For time-constrained problem-sets, particularly those with exponential DR curves, shortening tOR can significantly diminish the risk of an adverse outcome or, conversely, increase the probability of a positive outcome. The PreDICT system can improve tOR by improving the different components in multiple ways through, for example, increased certainty, decreased time, and decreased interventional risk through improved recommendations on actions and interventions through analysis of process and logistics within the prevailing risk-context. An additional note on equation 5; DC is a function of tDA (DC(tDA)) and not tDx (DC(tDx)) because tDA is the time at which the diagnostic certainty threshold is effectively applied in the problem-set.

Time-Constrained Problem-Sets: Definitions of "Time-Constraint/Time-Constrained"

The time of operational risk (tOR) is also key to understanding the definition of "time constrained" problem-sets. A time constrained problem-set could be any problem-set that has some pre-defined time at which critical decisions can no longer be made or actions taken to mitigate or avert the determinative risk or, conversely, realize benefit. An example would be a financial option to buy or sell a particular investment. An individual considering purchasing an option, or the holder of an option, must weigh potential benefit (profit), probability of realizing that profit (diagnostic certainty), and the cost of the option (interventional risk) in their decision to purchase or exercise the option. At some predetermined point in time, the option will expire and the ability to purchase or exercise the option will no longer exist. Alternatively, a problem-set could be time-constrained in some absolute term that humans generally agree to be "a short period of time" and, thus represent a time constraint. For example, a problem-set that played out over a single second, minute, hour, or day could be construed as time constrained.

However, what is more important is not the absolute time but rather the amount of time afforded or circumscribed by the determinative risk relative to the time of operational risk—the time required to mitigate or avert the determinative risk (or realize the relative benefit). The greater the ratio of tOR/tT the greater the time constraint or, stated differently, the greater the "risk density" of time or of the problem-set. Importantly, if tOR>1=tT or if tOR/tT>1=1, the determinative risk cannot be mitigated or averted. There is not sufficient time. This would be an impossibly time constrained problem-set that would require a different approach and solution to decrease tOR to less than tT if there was to be any probability of mitigating or averting the determinative risk. Let's examine an example of "time-constraint" through the ratio of tOR/tT. Stage 4 pancreatic cancer has a 5-year survival rate of approximately 3%. For the purposes of illustration, assume 97% of patients diagnosed with stage 4 pancreatic cancer will die exactly 5 years form the date of their diagnosis. Thus, for these patients the time terminal (tT) is 5 years. Also assume that for these patients, their survival beyond 5 years, either by mitigating or averting the stage 4 pancreatic cancer, will require the development of drug X. This means that a significant part of the operational risk for these patients is the development of drug X. And, not only the development of drug X but also clinical trials, FDA approval and/or emergency use authorization, manufacture and distribution, a course of multiple treatments, etc. This is a lot to accomplish in 5 years. The time of operational risk (tOR) will likely be close to if not exceed tT in this case. The point is that, with respect to time-constrained problem-sets, 5 years may not initially appear to be a significant constraint but, when compared to the time required to implement a meaningful intervention and for that intervention to take effect to mitigate or avert the determinative risk, the tOR, 5 years may represent a significant time constraint.

Another important point on the issue of "time constraint," we often know that a problem-set is time constrained or that it has the potential to be time constrained but the actual (or potential) time constraint is not always transparent to the decision maker. In some cases, decision makers may ultimately realize that there was no time constraint at all. This is an issue of diagnostic certainty involving 1) the correct identification of the problem-set from a given possibility/probability-set and 2) the correct diagnosis of the problem-set once it has been identified. A decision maker may be aware that there are multiple problems in their possibility-set. They may be aware that only one of these problems is time-constrained. However, if the decision maker decides (based on some level of diagnostic certainty and/or their subjective risk tolerance because of the potential or perceived consequence of the problem) that this single time constrained problem warrants due consideration, then the time constraint posed by this one possible (not necessarily probable) problem will constrain the entirety of their decision making. They have a time-constrained problem-set even if, in reality, no time constrained determinative risk exists.

Also important to consider is how the time-constraint imposed by an actual or potential determinative risk may be contextual rather than organic to the determinative risk and how a time-constraint posed by one DR and/or tOR may impose a time constraint on another DR and/or tOR. And, how the decision maker(s) who is/are subject to the time constraint may not be a primary component in the risk-context and problem-set. Consider the case of a U.S. servicemember with a headache and lightheadedness thirty minutes after being exposed to a close proximity blast from an enemy rocket fired at her base from an enemy convoy in the desert. The patient was in a bunker at the time of the blast and sustained no other injuries and did not lose consciousness. She now presents to the aid-station for evaluation by her unit's physician. After conducting an appropriate assessment, the physician is concerned, but is not certain, that she may have a mild traumatic brain injury (mTBI). This is often a challenging diagnosis to make and frequently requires hours to days of observation and reassessment to make a definitive diagnosis. The diagnosis is further complicated by multiple other stressors in the combat risk-context that can cause headache and lightheadedness—dehydration, inadequate nutrition relative to physical and mental exertion, poor sleep, mental, physical, and emotional stress, etc.

Once the risk of life-threatening intracranial pathology (such as a bleed) has been "ruled out" (reasonably removed from the medical decision maker's possibility/probability-set or differential diagnosis), this is a fairly straightforward medical problem-set characterized by a patient with headaches and lightheadedness that can be treated with low risk interventions. She may have a mTBI or she may just be, for example, dehydrated. The physician has sufficient diagnostic certainty relative to the low risk interventions to proceed with treatment and continue to monitor for mTBI over the next several days. So, the physician observes the patient for an hour while he provides IV hydration, a snack, and Tylenol and then prescribes the patient a period of "brain rest", the treatment for mTBI. Brain rest essentially consists of lying in a darkened room without stimulation such as physical stimulation, screens, mental exertion, etc. This treatment, while seemingly anodyne, is critical to allow the brain to heal and to avoid long term sequelae of mTBI such as memory loss, personality changes, and other mental and emotional signs and symptoms. The patient is to return to the aid-station in twelve hours for re-evaluation. If, at that time, she demonstrates continued signs and symptoms of mTBI, the physician will recommend evacuation to a higher level of care for ongoing evaluation, treatment, and recovery.

So far, this does not appear to be a particularly challenging problem-set and the determinative risk does not appear to present a significant time-constraint. But, now consider the problem-set from the perspective of a different decision maker, one who is non-medical and not a primary component of the medical problem-set involving the patient. The theater task-force commander must determine the response to the rocket attack. A critical risk-variable in the commander's decision making is whether or not the service member has a mTBI. A mTBI sustained in combat and due to enemy action is recognized as a battle injury and qualifies for a Purple Heart in the same way that the patient in this example would qualify for a Purple Heart if she sustained a life-threatening injury from a piece of shrapnel in the rocket attack. Since the attack, the task force has identified a suspicious convoy in the vicinity of the base that they believe launched the rocket and the commander is considering authorizing a drone strike on the convoy. The convoy is assessed to be traveling towards a city about an hour away but, until that time, will be in "green terrain" (an open, unpopulated area with a low risk of collateral damage from the drone strike). Thus, the commander has one hour to make a decision (tDA) and execute the strike (tI+tIE). One hour from now is effectively the time terminal (tT) in the commander's time-constrained problem-set. Furthermore, the convoy is assessed to be carrying a proxy militia force for a near-peer U.S. adversary with at least two embedded intelligence officers from the intelligence service of the near-peer adversary. Striking the convoy, and particularly killing those intelligence officers, has significant strategic implications, it may precipitate major armed conflict. However, if the strike is justified in the eyes of the international community and according to relevant laws of armed conflict, this consequence is unlikely. Not striking the convoy also has significant implications. Right now, the commander has the opportunity and the tactical initiative to carry out the strike and remove this threat from the battlespace, send a deterrent message to the adversary, and, potentially, conduct a proportionate response under the standing rules of engagement. This could save lives in the future and improve the United States' strategic position in the region. Not striking could embolden the enemy. But, to justify the strike the commander must have some threshold of diagnostic certainty (preferably a definitive diagnosis from a medical professional) that the patient has a mTBI.

Even though the commander is not a primary component of the patient's medical problem-set and even thought the determinative risk in the problem-set (potential mTBI) does not directly prescribe a time-constraint (though the patient, if she has an mTBI, is at increased risk of long term sequelae if brain rest is not implemented to mitigate or avert those risks) the commander is confronted with a time-constrained problem-set that is framed (and constrained) by her mTBI problem-set. The (potential) determinative risk of the mTBI has an associated tDx that, in this risk-context, directly affects the tDx and time of operational risk for the commander's convoy determinative risk problem-set. In this risk-context, the problem-set posed by the patient and her potential mTBI shapes the time-constraint of the commander's problem-set focused on the convoy. From the commander's perspective, the time terminal (tT) is one hour from time now. The commander's time of operational risk consists of:

Time to meaningful contact (tMC): This has been accomplished. The commander understands the nature, scope, and risk-variables of the problem-set.

Time to diagnosis (tDx): The commander has reached a diagnostic certainty threshold on part of the determinative risk (the convoy) but still requires a key piece of information, does the servicemember have a mTBI. In other words, from the commander's vantage point, the convoy is a determinative risk. If the convoy launched a rocket that resulted in a mTBI to a US servicemember it is a sufficiently high risk to justify the high-risk intervention of a drone strike under the standing rules of engagement. If it did not cause a mTBI it is not a sufficiently high risk to warrant the high-risk intervention of a drone strike.

Time to decision to act (tDA): This decision has already been made. If mTBI, strike. If no mTBI, no strike.

Time to intervention (tI): This is the time required to launch the drone, for the drone to fly to and acquire the target (the convoy), for the drone to release the munition, and for the munition to impact and destroy the target. Let's assume that this has been accomplished and the convoy is being watched by an armed drone.

Time to intervention efficacy (tIE): Time from munition impact until kinetic effects are realized. This is a very short period.

The rate limiting step is the tDx for mTBI and this time will be greater than one hour. The commander is evaluating a problem-set with a tT of one hour from now. Because tDx factors into the commander's tOR for mitigating or averting the risk posed by the convoy, the tOR will be greater that one hour. Time of operational risk is greater than time terminal. The convoy will reach the city and be out of green terrain, thereby precluding the drone strike, before the commander (or physician or patient) have a sufficient diagnostic certainty threshold to diagnosis mTBI. If the commander did not require that the patient have a definitive mTBI diagnosis to justify and launch the drone strike then the tOR would have been well within the tT of one hour and the convoy would have been effectively neutralized. This hypothetical example was intended to illustrate how problem-sets can overlap and interact in a particular risk-context to impose time-constraints on decision makers that are not obviously organic to the immediate problem-set. If the patient in our example had suffered a possible mTBI playing intramural soccer at college back in the US, her (potential) determinative risk of mTBI would not have these same secondary effects on a non-primary component of her mTBI problem-set. PreDICT will markedly improve the diagnostic efficiency (accuracy and speed of diagnosis) of pathology such as mTBI. Consequently, it has the ability to enhance decision making in the primary problem-set (mTBI) in the example above as well as in the secondary problem-set (convoy drone strike).

The mTBI example above also illustrates another important point about tOR and time constraints, the time to diagnostic certainty threshold (tDx) is influenced by IR. If the IR is low, the diagnostic certainty threshold required to proceed with that intervention is generally low and has a relatively short tDx. If the IR is high, the diagnostic certainty threshold required to proceed with that intervention is generally high and has a relatively long tDx. (This, of course, also depends on where you are in the time sequence of the problem-set, the consequence of the terminal risk/outcome, and the risk-density of time. In a high-risk problem-set with a high risk-density of time, a decision maker may be willing to accept a high-risk intervention with little diagnostic certainty if only because it is the only option available given the apparent time remaining in the problem-set.) From the standpoint of the physician treating the patient, and viewing this as a purely medical problem-set, the IR for mTBI is low (brain rest) so a low level of diagnostic certainty, and correspondingly short tDx, is required to make a decision to act and implement treatment. If the patient is ultimately determined to not have a mTBI, there is no adverse medical consequence to the patient from brain rest. Conversely, if the patient does have an mTBI and does not undergo brain rest early, she is at higher risk of morbidity from the mTBI. (Note: this also serves to illustrate the tIE of brain rest.) Now, from the perspective of the commander authorizing a drone strike, he requires a higher level of diagnostic certainty regarding the same determinative risk precisely because he is weighing a higher risk intervention based on the same determinative risk. And, this higher level of diagnostic certainty requires more time to attain, it has a longer tDx. In summary, the available interventions, and their associated risks, for a given determinative risk, can impose a time constraint by increasing the required diagnostic certainty threshold which, in turn, increases tDX, which, in turn, increases tOR and increases the ratio tOR/tT.

Interventional Risk

Interventional risk includes the risk of all interventions, for the purpose of increasing certainty (diagnostic interventions) and towards mitigating or averting the determinative risk (therapeutic interventions). As a general rule, critical decision makers do not apply benefit in time-constrained problem-sets. In other words, the interventions are not inherently beneficial unto themselves. They are beneficial by virtue of their potential to yield a relative benefit in the problem-set. Decision makers apply the risk of intervention to the determinative risk and problem-set with the goal of yielding a relative benefit (RB). For example, a computed tomography (CT) scan is not inherently beneficial, it carries risk in the form of potentially cancer-causing radiation, direct economic cost, opportunity costs, etc. However, in the setting (problem-set) of a patient with right lower quadrant abdominal pain concerning for appendicitis, it can increase diagnostic certainty and, in turn, relative benefit to the patient. The diagnostic certainty yielded by the CT scan decreases the probability that an actual appendicitis is misdiagnosed or that a presumed appendicitis (but normal appendix) undergoes an unnecessary surgical procedure (appendectomy).

Interventions generally entail risk in some form or fashion. These may be inherent risks, such as the risk of morbidity and/or mortality inherent in many medical interventions, these risks may involve the probability of the success or failure of the intervention, these risks may be in the form of opportunity cost or monetary costs, or these may be the risks of adding degrees of freedom to an already complex problem-set, such as might occur by using a military intervention to solve a non-military problem-set at the risk of creating multiple additional time-constrained problem-sets. Alternatively or additionally, these interventional risks might manifest or come to bear in any number of ways not enumerated here. Some interventional risk, such as the risk of failure of the intervention to have the desired consequence, is captured by the concept of diagnostic (un) certainty—the level of certainty a decision maker has about underlying determinative risk will affect their ability to match the most risk and efficacy appropriate intervention to the problem-set. Other interventional risk is captured directly by what is termed here as interventional risk (IR).

Interventional risk (IR) is a function of determinative risk (DR) in the sense that DR circumscribes and defines the problem-set and, in turn, generally constrains what interventions could or would be applied. For example, if the determinative risk is pancreatic cancer then options for intervention will generally fall in the realm of medicine and not routinely include the use of military force to mitigate or avert the DR. Applicable interventions based on the DR underlying the problem-set will then have associated interventional risk. However, it is important to understand that interventions and associated interventional risk seemingly unrelated to the DR may be incurred incidentally or collateral to applying an appropriate or optimal intervention. For example, a patient is at hospital A with a severe head injury requiring a neurosurgeon to urgently perform a procedure. The nearest neurosurgeon is at hospital B 100 miles away and the patient must be transported by helicopter. In this example, the interventional risk of the neurosurgical procedure includes the risk of the helicopter transport as it is, effectively, a required part of the neurosurgical procedure. (Of note: it is also part of the time of intervention (tI) and, in turn, the time of operational risk (tOR).) These types of scenarios are common for medical problem-sets in the military combat and other austere risk-contexts.

Figure 9A:
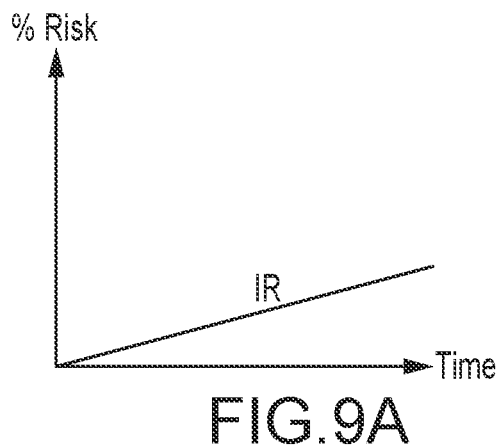
Figure 9C:
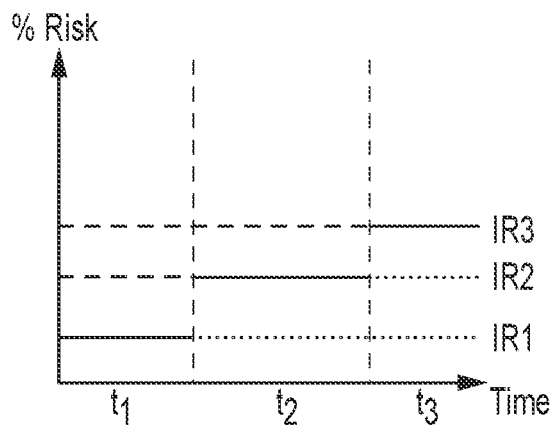
Figure 9B:
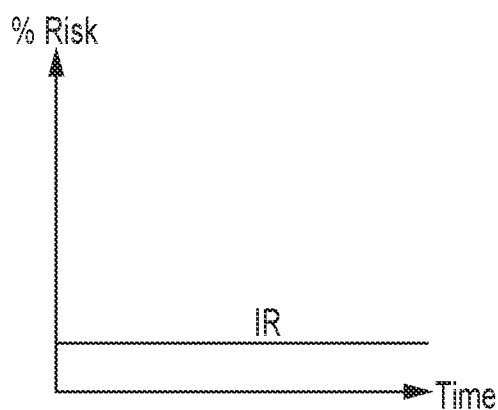

FIGS. 9A-9C show representative IR curves as functions of time, though they are by no means a compete or exhaustive representation of all possible IR curves. There are several general concepts demonstrated. The first is that the absolute interventional risk will generally not decrease with time (though, the relative risk of intervention(s) may well decrease with time as considered from different perspectives such as, "this is a high-risk intervention but we are moments away from a high consequence outcome and have no other options and little or nothing to lose . . . " Note: in this example the "relative risk" of intervention will also be modified (decreased) by the (high) level of diagnostic certainty with which it is applied). Interventional risk curves will generally increase with time or remain flat (slope=0) as functions of time (see FIGS. 9A-9B). A patient who is bleeding from an extremity wound and progressing towards hemorrhagic shock and death is an example where the risk of intervention increases with time. In the early stages after the onset of the determinative risk (the bleeding wound) the patient may only require a tourniquet and medications such as tranexamic acid (TXA) to mitigate the DR followed by a procedure to avert it. As the DR progresses the patient will require more interventions, such as blood products, and thus more interventional risk to mitigate and avert the DR. The previous example of the aircraft engine failure might be represented by a flat IR curve (see FIG. 9B)—the engine malfunctioned, the source of that malfunction is stable, there is one possible intervention to fix the malfunction. Note, this does not account for other possible "interventions" available to the pilot and passengers trying to avoid a terminal outcome of a fatal impact, such as parachuting out of the aircraft. The second concept is that interventional risk will often be "quantized;" it will change with time in a "stairstep" fashion (see FIG. 9C) This is because each intervention has some inherent risk associated with it and, as the DR progresses and more interventions are required, the IR at different points or periods in time will be additive (not necessarily in direct proportions (i.e., 2+2 may be less than 4 or it may be greater than 4)), synergistic, and/or multiplicative. Also, just because an interventional risk is not risk-optimal at a given point or period of time in the problem-set does not mean that it cannot be applied. However, the outcome may be that the intervention is effective at mitigating or averting DR but incurs an unnecessarily high degree of interventional risk to accomplish the effective outcome. Alternatively, the interventional risk applied may not be sufficient to effectively mitigate or avert the DR while still incurring risk (without yielding any relative benefit). FIG. 9C depicts three levels of interventional risk (IR1, IR2, and IR3). Solid portions of the IR curves show where the interventional risk is "risk optimal" relative to the DR. Dashed portions of the IR curves show where the interventional risk is effective but unnecessarily high. Dotted portions of the IR curves show where the interventional risk is ineffective and IR is incurred without RB. Also important to consider, the operational risk associated with an intervention (tI, tIE) and where the DR is in its progression are critical considerations in the risk calculus of determining what IR or bundle of IR is most risk appropriate and effective. If an intervention has a relatively long tI and/or tIE, then a decision maker may be required to implement that intervention before it is apparently "risk optimal." Considering FIG. 9C as an example, if the problem-set is current in the period of time "t2" and IR2 and IR3 each have a combined (tI+tIE)>t2 then the decision maker needs to implement IR3 even though it appears to be an overly high risk intervention for that period in the problem-set. Time constrained problem-sets where the implementation and effects of interventions are separated by significant periods of time (relatively long tI and/or tIE) present significant critical decision-making challenges. The PreDICT system has the capability to match the risk optimal interventions to the specific level of DR at a specific point in time in a given risk-context at machine speeds with a cognitive bandwidth that exceeds human capabilities. Also important to understand is that the PreDICT system not only recommends (or autonomously applies) the risk optimal intervention at the optimal point in time, it also recommends (or performs) the optimal sequencing and logistics to maximize the efficiency, relative to both time and interventional risk, of the intervention.

Risk of Diagnostic Uncertainty (Benefit of Diagnostic Certainty) Curves

This section discusses the Risk of Diagnostic Uncertainty and the Benefit of Diagnostic Certainty (DC), which is the complement of the risk of diagnostic uncertainty (DU) (DC(t)=1−DU(t)), similar to discussing PB(t) as the complement of DR(t) in a previous section. Diagnostic certainty is the probability that the critical decision maker has identified 1) the correct DR curve (the correct risk within the possibility-set and corresponding terminal risk) and 2) has correctly identified the "shape" of the DR curve or time function describing the DR curve (the risk at the present time, the risk at any future time, and the time terminal and time constraint defined by the DR curve).

At the time of onset of the DR (t0) the corresponding diagnostic certainty (DC) is zero (DU(t0)=100%). Time terminal (tT) and beyond is the only point in the problem-set (and period following) at which DC may be 100% (or DU may be 0%) because at this point the terminal outcome has been realized and, so long as that terminal outcome is completely transparent to the critical decision maker, they then have, or could have through literal or figurative autopsy of the problem-set, 100% certainty as to the determinative risk and its nature and characteristics. Between the onset of the determinative risk (t0) and just until time terminal (tT), diagnostic certainty will be greater than or equal to zero and less than 100% (0</=DC(t0+x to tT−y)<100, where x and y are positive). There are multiple reasons why DC may be at or near zero for a prolonged period throughout a problem-set, such as an insidious DR that does not rise to the level of sensory perception or cognition or, simply, because the critical decision maker(s) are not, for whatever reason, aware of it. Whatever the case, this would manifest as a prolonged time to meaningful contact (tMC) followed by some period of time to diagnostic certainty (tDX) during which decision makers sought to attain a threshold of diagnostic certainty to initiate action.

Figure 10:
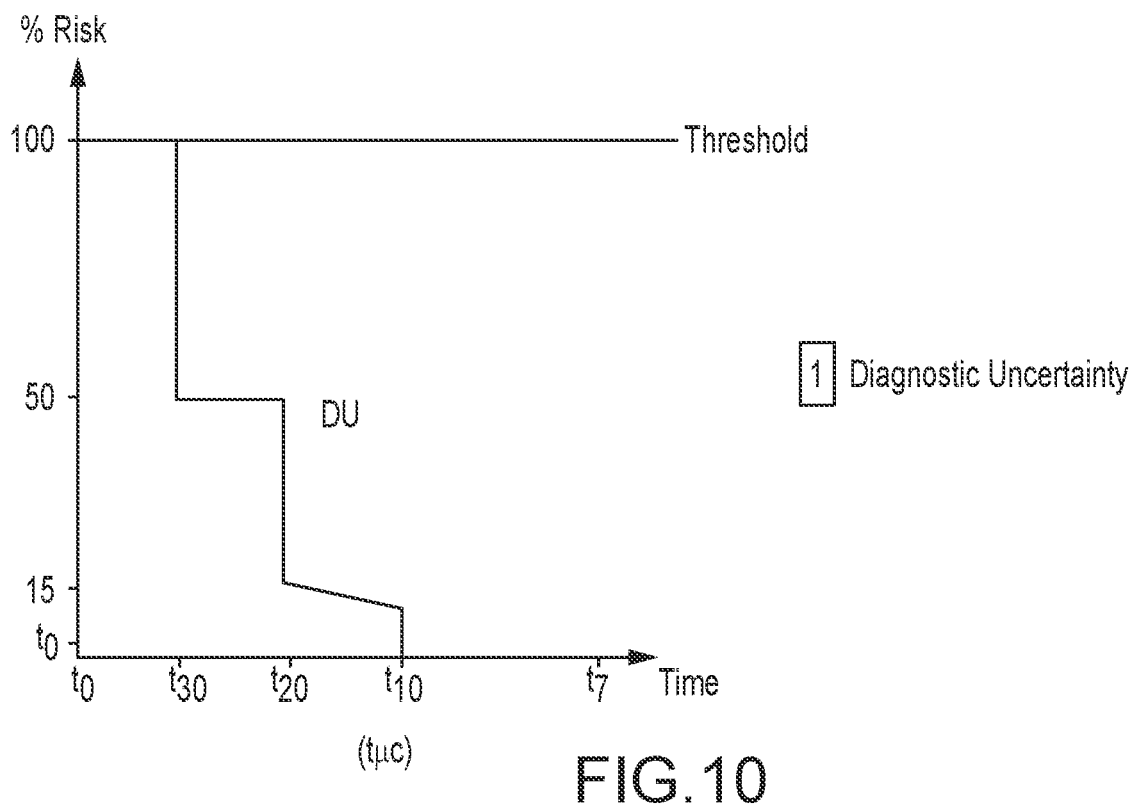

As with other curves and functions that we have discussed, diagnostic uncertainty (DU) functions/curves (and diagnostic certainty (DC) functions/curves) can take multiple forms. FIG. 10 depicts what a simplified diagnostic uncertainty (DU) curve might look like from the perspective of a trauma surgeon at a Level I Trauma Center receiving an injured patient with no notice. At t0 the patient falls 8 ft off a ladder and lands on his left side/back. At this point in time the trauma surgeon, who will ultimately be the critical decision maker in this problem-set, has no awareness that this even occurred and has a diagnostic certainty of zero (DC(t0)=0). At ten minutes from the time of injury (t10) the patient is brought to the emergency department by his friends and is encountered by the trauma surgeon. This is the time of meaningful contact (tMC). At this point in time the trauma surgeon rapidly ascertains, through observation and discussion, that the patient is a healthy 25 year-old male who fell 8 ft off a ladder and landed on his left back/side and "had the wind knocked out of him." He is awake, alert, oriented and generally appears stable. The patient complains of significant pain in his left chest and flank but otherwise denies any other injuries, complaints, or loss of consciousness. The patient has no significant past medical or surgical history. At this point in time (tMC) let's assume that the trauma surgeon has 50% diagnostic certainty regarding the presence of two potential life threats that would be likely to exist in this patient's presentation; a splenic injury and/or pneumothorax.

The trauma surgeon has multiple decisions to make but the fundamental underlying critical decision is, "does this patient have a life-threatening injury(ies) (splenic injury and/or a pneumothorax) that requires intervention to mitigate and avert the threat?" In the risk-context of a Level I Trauma Center, the trauma surgeon has multiple diagnostic interventions available to answer that question relatively rapidly. The trauma team gets the patient's vital signs, performs a physical exam and an ultrasound exam (E-FAST), gets a bedside chest x-ray, and a point of care hemoglobin. Collectively, these diagnostic interventions take 10 minutes to acquire and result, with results obtained at t20, 20 minutes from the time of injury. During this 10 min interval diagnostic certainty did not appreciably change except for the information extracted through clinical assessment, which revealed the patient is largely stable and likely has left sided rib fractures. At 20 minutes from injury (t20), when the diagnostic interventions are resulted, they reveal that the chest x-ray and ultrasound are negative for evidence of pneumothorax, the ultrasound shows a small amount of free fluid in the abdomen (intraperitoneal free fluid), the point of care hemoglobin is within normal limits, and vital signs are grossly stable and not indicative of acute decompensation. Now, at t20, diagnostic uncertainty drops to, let's say, 15% regarding the diagnosis, a likely injury to the spleen or its blood supply.

The question now becomes, "has a diagnostic certainty threshold been reached to intervene?" There are several possible courses of action to intervene in order to mitigate or avert the problem-set of a splenic injury. A mitigating intervention is to administer blood to counteract the internal bleeding resulting from the injury. If the splenic injury is not severe, it may be sufficient to administer blood while the body's internal mechanisms (blood clotting) stop the bleeding (avert the risk) and then observe the patient for a period while they are most at risk of decompensation. If the injury is severe and resultant bleeding outpaces the body's compensatory mechanisms and reserves, then surgery (to remove the spleen and tie off blood vessels) is required to avert the underlying determinative risk (bleeding to death from the splenic injury). Many physicians and surgeons would agree that the patient has met the diagnostic threshold to administer blood at this point. In a stable patient, such as this one, in the risk-context of a Level I Trauma Center most physicians and surgeons would likely agree that surgery (an exploratory laparotomy) is NOT indicated at this point—that is to say that the diagnostic certainty threshold has not been met to apply the (high) risk of intervention of surgery. Thus, the decision is made to get another point of care hemoglobin, start blood, and take the patient for a computed tomography (CT) scan of the abdomen-pelvis with intravenous (IV) contrast to more fully evaluate the spleen and gain more diagnostic certainty.

At time t30, thirty minutes from the time of injury, the CT scan is complete. It demonstrates a Grade IV splenic laceration with significant intraperitoneal free fluid consistent with acute bleeding. The patient requires emergent surgery. The repeat hemoglobin has been resulted and demonstrates a two-point drop from the initial hemoglobin. Also, the patient's heart rate steadily increased and his blood pressure steadily dropped during the ten-minute interval from t20 to t30. He now appears pale and is sweating (diaphoretic). The trauma surgeon is now confronted with an unstable patient with a CT scan demonstrating an underlying splenic injury requiring surgery. Diagnostic uncertainty is now approaching zero and the diagnostic certainty threshold for intervention has been met (and likely exceeded at a level of 99+% diagnostic certainty based on information presented). Fortunately, the patient is receiving blood to mitigate the risk. However, the time of intervention efficacy (tIE) for the blood may not have yet been reached but, at least, the patient and the trauma team will not be behind the curve and the patient is on track to receive excellent care.

This scenario is a simplified example of the complexities of a trauma scenario and associated diagnostic (un)certainty and decision making. It is captured in FIG. 10. A few additional points: 1) Diagnostic uncertainty and certainty curves will frequently demonstrate some type of "stair step" pattern, which demonstrates the way in which new information leading to decreasing diagnostic uncertainty or increasing diagnostic certainty is often quantized. Critical decision makers are frequently confronted with new information that effects their level of diagnostic (un)certainty in aliquots. However, some new diagnostic information will be obtained in more of a "smoothed out" fashion, such as through clinical observation of a patient over time, that will often be a reflection of the shape of the underlying DR curve (reference FIG. 5A—the DR curve and DU curves move in opposite directions with the same shape). 2) There is almost always some time lag between the diagnostic certainty of the critical decision maker and the actual state of the underlying determinative risk. For example, if the point of care hemoglobin test (to look for evidence of bleeding) takes 5 minutes to perform and result, then, at the time it is resulted, it provides the decision maker information about the patient's hemoglobin level 5 minutes ago, not right now when it is resulted. This contributes to the quantized stair step nature of diagnostic certainty—enough diagnostic certainty is obtained to guide some future diagnostic step, then that step is taken and time elapses for it to be resulted during which little or no more diagnostic certainty is obtained, then that step is resulted and you realize another gain in diagnostic certainty (or not), and this continues until some threshold of certainty is reached.

One of the critical capabilities of the PreDICT system is to decrease the "stair step" pattern of diagnostic (un)certainty curves by markedly shortening the plateaus (or relative plateaus) in the curve by obtaining near immediate results of diagnostic interventions to include interpretations of standard-of-care diagnostic interventions, multiple other sensor devices, such as wearables, and through performing non/minimal contact artificial intelligence "clinical observation." The result is that the PreDICT system will decrease tDX and, in turn, tOR. While the patient in our example has a high likelihood of survival, this likelihood could have been further enhanced if the diagnostic certainty threshold to take him to the operating room was reached at t20 rather than t30—the absolute risk would have been lower (he was not yet decompensating at t20) and the risk density of time would have been lower (more time to mitigate and avert the underlying risk (splenic injury)) before the terminal outcome (death due to hemorrhage) at time terminal. The result of intervention at t20 rather than t30 would have been increased relative benefit (RB).

Putting it all Together: Equation 6

Figure 11:
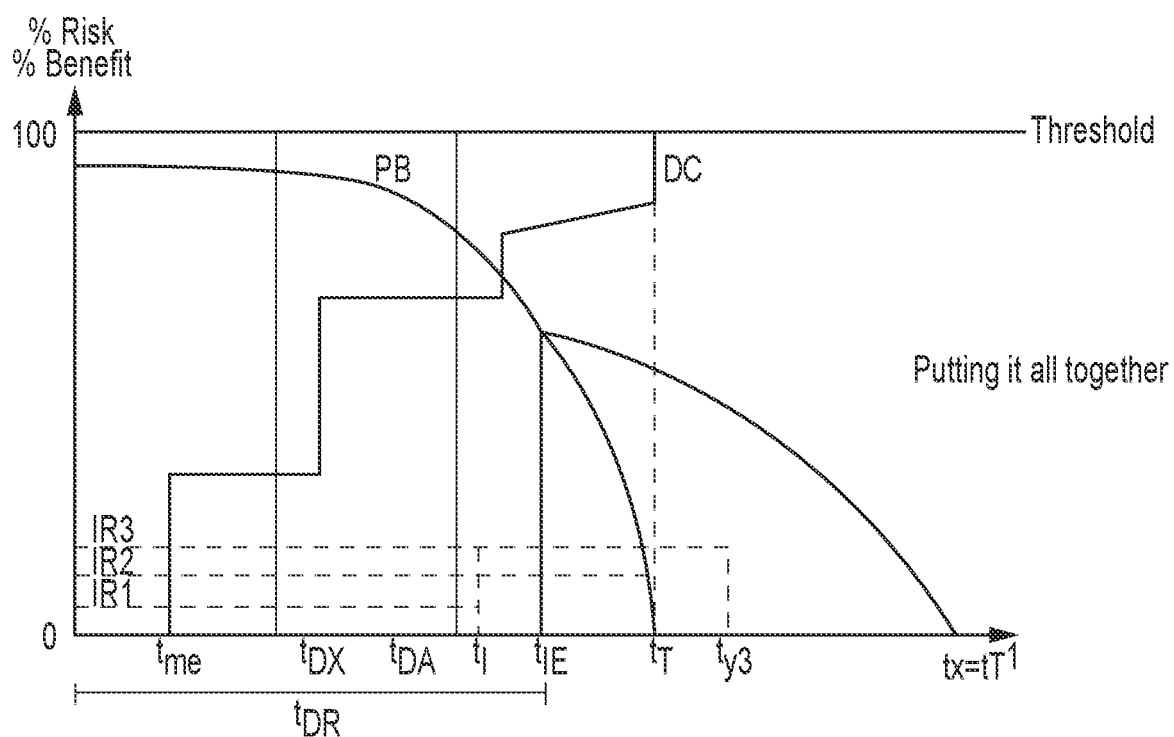

FIG. 11 depicts functions and curves that we considered above combined into one graph, including operational risk and an example of mitigating the determinative risk. This figure is effectively a graphical representation of a time-constrained problem-set. It includes the four fundamental risk-variables of a time-constrained problem-set: 1) Determinative risk (DR), 2) Risk of Diagnostic Uncertainty (DU), 3) Interventional Risk (IR), and 4) Operational Risk (OR). Because we are primarily concerned with relative benefit (RB), determinative risk is depicted as its complement, potential benefit (PB=1−DR) and diagnostic uncertainty is depicted as its complement, diagnostic certainty (DC=1−DU).

Earlier, we examined equation 5:

$$RB(tOR) = [DC(tDA) \times PB(tOR)] - IR(tI)$$

Equation 5 gives the relative benefit at a specific point in time (tOR) within the problem-set. What we really want to know from a critical decision-making standpoint is, what is the total relative benefit, for the problem-set and into the future, yielded by decisions and actions in the present (tDA and tI)? In a medical problem-set, we may wish to calculate RB out to the expected natural life of the patient. This requires solving equation 5 while considering some of the risk-variables over time; solving them as integrals. This yields equation 6:

$$RB(tOR) = \left[DC(tDA) \times \int_{tOR}^{tX} PB(t)dt\right] - \left[\left(\int_{tI1}^{tY1} IR1(t)dt\right) + \ldots + \left(\int_{tIn}^{tYn} IRn(t)dt\right)\right]$$

Where:

tX—
  Mitigating DR: tX=tT'
  Averting DR: tX=tR tY—
  tY=the time at which an interventional risk (IR) "extinguishes" or a future time selected as a boundary on the problem-set, whichever comes first.
  Note: Equation 6 is only one possible quantitative interpretation of the time constrained, expected value, optimal stopping problem. For example, the equation could also be expanded to account for the determinative risk from t0 to tOR as follows:

$$RB(tOR) = \left[DC(tDA) \times \int_{tOR}^{tX} PB(t)dt\right] - \left\{\left[\left(\int_{tI1}^{tY1} IR1(t)dt + \ldots + \left(\int_{tIn}^{tYn} IRn(t)dt\right)\right] + \left[(100 \times tOR) - \left(\int_{t0}^{tOR} PB(t)dt\right)\right]\right\}$$

This interpretation accounts for the latent DR from the DR onset until the DR is successfully mitigated or averted. Ultimately, the quantitative interpretation used to resolve any time-constrained problem-set will depend on factors specific to that problem-set. Furthermore, whatever specific quantitative interpretation is used, it will be important to normalize relative benefit (RB) results against an empiric or otherwise determined baseline or comparative example for that quantitative interpretation.

Within the time-constrained problem-sets we have been discussing there are essentially two distinct optimal stopping problems: 1) High Diagnostic Uncertainty and 2) Low Diagnostic Uncertainty. The high diagnostic uncertainty problem occurs when the critical decision maker has relatively low diagnostic certainty about the underlying DR and confronts the critical decision maker with the following questions:

Is it better to intervene earlier with more diagnostic uncertainty risk or is it better to intervene later with less diagnostic uncertainty risk at the potential cost of increasing determinative risk during the interval required to attain the additional diagnostic certainty?

How does intervening later affect the time of operational risk (tOR) relative to time terminal (tT)?

Will increasing DR and risk-density of time require higher interventional risk (IR) to mitigate or avert DR if IR is applied later?

Stated differently, is (DR(t2)−DR(t1)) greater than, less than, or equal to (DU(t1)−DU(t2))? AND/OR does a later intervention result in tOR>tT or an otherwise unacceptable risk-density of time? AND/OR will a delay in intervention require higher interventional risk (IR)? These considerations will determine the optimal point in time for the function DC(t) and, in turn, the diagnostic certainty threshold for intervention. Note, if the delta in DR and DU is equivalent for the time interval then earlier intervention is favored because it decreases the risk-density of time and protects against the risk of requiring higher IR at the future time.

The low diagnostic uncertainty problem occurs when the critical decision maker has a relatively high degree of certainty about the underlying DR, such as the terminal outcome of DR and the timeframe at which it will occur (time terminal, tT), and confronts the critical decision maker with the following questions:

Is it better to apply a higher risk intervention now or is it better to apply a lower risk intervention later at the risk of the increased DR in the interval?

Do the constraints of tOR for the lower risk intervention relative to tT even make the future, lower risk intervention a viable option or is tOR>tT or the risk-density of time unacceptably high?

The existence of this low diagnostic uncertainty decision and question seemingly contradicts an earlier statement that interventional risk (IR) generally increases with time. It does generally increase with time and the existence of this decision does not contradict that. What this decision considers is the time cost of transitioning from one (higher) risk-context to another (lower) risk-context. We will discuss risk-context in more detail below but, for now, understand that determinative risk (DR) is effectively the same, without intervention, irrespective of risk-context. Also, understand that within any given risk-context the interventional risk required to mitigate or avert the underlying DR will generally increase with time. However, whether it does or does not, the same intervention required at time "X" may carry a different level of interventional risk (IR) in one risk-context versus another. For example, at tX a patient requires surgery to repair a hemorrhaging blood vessel after suffering penetrating trauma. The interventional risk (IR) associated with the procedure will be lower at a Level I Trauma Center in the US with extensive resources in a modern, sterile hospital facility than it will be in a rapidly established temporary medical facility in Afghanistan with a small surgical team working out of nick sacks. The Level I Trauma Center is a different risk-context than the small medical facility in Afghanistan. This is an extreme example but, another example where this decision plays out every day in the US, and has already been made at a system level, is the interplay between emergency medical services (EMS) and specialty medical centers for time critical illness and injury such as Trauma, STEMI (cardiac), and Stroke centers. When patients encountered by EMS meet certain criteria (i.e. there is some relatively high level of diagnostic certainty relative to the EMS medical providers' expertise) for the conditions mentioned above, those patients are transported directly to the relevant specialty center even if it means bypassing a closer medical facility and increasing (at least part of) the time of operational risk and potentially allowing the underlying DR to progress during the increased transport time. The critical decision has been made to implement a system that trades the risk of time for lower interventional (and other risk) by placing the patient in a more favorable risk-context (the relevant specialty center). The PreDICT system has the capability to improve or alter this paradigm by both favorably altering the risk-variables within the problem-sets across all risk-contexts (i.e.—decrease risk associated with treatment at a non-specialty center vs a specialty center) and by computing the risk-variables in the decision to bypass a closer hospital for a specialty center at an individual patient level (rather than a systems level) and at machine speeds.

Risk-Context:

The risk-context is the context in which a determinative risk (DR) manifests and this context, in turn, affects the risk-variables, particularly operational risk (OR), and, together with the determinative risk, defines the problem-set. Another way to understand this is that a particular problem-set is defined by a determinative risk in a particular risk-context. Risk-context has three domains: 1) Environment, 2) Systems, and 3) Components. The environment domain is shaped by broad forces such as climate, weather, terrain, social and cultural factors, politics, economics, security, and certain infrastructure. The systems domain considers systems that have been established to address, in full or part, determinative risks and/or other types of risk. These include the military, EMS and health systems, law enforcement, fire departments, emergency management bureaucracies, educational systems and initiatives, communications and power systems, FEMA, NOAA, DOE, and multiple other governmental agencies, non-governmental organizations (NGOs), private industry, and other civic, religious, or other entities/systems that exist to address specific risks or areas of risk. The component domain includes those components (human and material resources) that are directly part of and required to resolve the problem-set and mitigate or avert the underlying determinative risk. For example, for a patient experiencing chest pain due to a heart attack at home these components include the patient, the ability to communicate and activate the EMS system (a phone to call 9-1-1), transport to a STEMI (cardiac) center with medical care in route (an ambulance staffed with paramedics), and, upon arrival to the hospital, doctors, nurses, techs, clerks, medications, and specialized equipment to mitigate and avert the underlying risk (resolve the coronary artery blockage causing the heart attack). Components and systems have both task-specific expertise (humans) and capability (materials) and operational expertise (humans) and functionality (materials). Task-specific expertise entails the knowledge, skills, and critical decision making that component humans or systems apply to mitigate or avert the determinative risk. Task-specific capability refers to the task-specific capability of material and other resources that are implemented to mitigate or avert determinative risk. Operational expertise entails a broad and functional understanding of the risk-context (system and environment) and a decision-making framework that, together, potentiate the optimal application of task-specific expertise to mitigate or avert the determinative risk within that risk-context. Operational functionality is the principle that components and systems align with other domains of the risk-context to optimally provide an intended function to mitigate or avert risk. The environment domain determines what system and component domains can be supported. The system domain shapes the components and/or the components shape the system. Ultimately, the components coalesce within the system to (ideally) mitigate and avert the underlying determinative risk and resolve the problem-set.

Risk-contexts exist across a spectrum from predictability risk-context (PRC) to adaptability risk-context (ARC). In a predictability risk-context (PRC), components and systems are purposefully trained and designed to manage specific types of determinative risk within an environment under a certain range of conditions. Components have the task-specific expertise and capability to mitigate or avert the determinative risk and the operational expertise and functionality to optimally apply the task-specific expertise or capability in the system and environment. Likewise, the system collectively has the task-specific expertise and function to support components in mitigating or averting determinative risk and the operational expertise and functionality to optimally do so within the range of environmental conditions for which it is intended. Decision makers in a PRC are primarily dealing with known-knowns and known-unknowns. At the extreme of an adaptability risk-context (ARC), the components and systems required to mitigate or avert the determinative risk do not exist and the environment cannot, or does not easily or rapidly, support their training, design, and/or implementation. There are multiple permutations of risk-context between the extremes of predictability and adaptability. Generally speaking, a risk-context trends towards predictability when the necessary component expertise and capabilities to mitigate or avert the determinative risk are confronting the determinative risk within a system purpose built to mitigate or avert the determinative risk under environmental conditions for which the components and systems were trained, designed, and implemented to optimally function. A risk-context trends towards adaptability the less these characteristics are present. This occurs when task-specific expertise or capability does not align with the determinative risk, operational expertise does not align with the system or environment, the system does not align with the components or environment, or the environment is highly dynamic and/or presents conditions that are outside the intended parameters for optimal component or system function. From the standpoint of a decision maker, an adaptability risk-context has many more degrees of freedom affecting the fundamental risk-variables of the problem-set that must be recognized, considered, and computed in order to optimally mitigate or avert the underlying determinative risk. Decision makers in an ARC may be dealing with known-knowns and known-unknowns but they are also dealing with many unknown-unknowns and variables and cause-and-effect relationships that are opaque or unknowable, at least within the time constraints of the problem-set.

A key point for decision makers to understand is that expertise, capability, and function are contextual and, consequently, to expertly and optimally resolve a problem-set the decision maker(s) require not only expertise regarding the determinative risk but also expertise regarding the risk-context in which the determinative risk is nested. Many problem-sets may not be optimally resolved not because decision makers lacked expertise related to the determinative risk but because the expertise was applied in a risk-context for which it was not developed or intended. This can occur through a failure of recognition of a change in risk-context or a failure of acceptance of a change in risk-context. In either case, it is a failure of adaptability that humans, and perhaps more so experts, are susceptible to. Expert components (decision makers) in a problem-set will have a mental model of other components, of the system, and of the environment. This mental model is developed through experience. Within this mental model they will execute habit patterns in response to specific risk stimuli. These habit patterns have developed in a specific risk-context, and mental model, to react to and resolve specific risks. In medicine, these habit patterns are termed "scripts" and can be thought of as what we frequently refer to as standards-of-care. The standard of care for a particular determinative risk is the habit pattern that relevant experts know (or believe) will produce the highest probability of an optimal outcome for a specific determinative risk in a specific context. There are multiple recognized cognitive errors in medicine and other human domains where decision makers apply a mental model, often that they have developed through experience, that does not align with the problem-set they are confronting. Subsequently, they execute habit patterns corresponding to the mental model and not the actual problem-set. When the risk-context changes and corresponding mental models and habit patterns to do not, decision makers are susceptible to the liability of negative habit pattern transfer—a habit pattern with a salutary effect in one context is applied in another context and either does not have the intended outcome or has a negative outcome.

Consider a 20 year-old healthy male with a gunshot wound to the abdomen. Imagine this patient in the risk-context of major metropolitan area in the United States on a "normal" day. Now, imagine this same patient in a different risk-context, on a mountain in Afghanistan in the middle of a firefight at night. The determinative risk is the same in each scenario but the risk-contexts and, in turn, the problem-sets are very different. Let's consider the problem-sets through the lens of the trauma surgeon, who is the expert and decision maker ultimately responsible for mitigating and averting risk to the patient. His/her goal is to minimize the time of operational risk (tOR) and successfully intervene to avert the determinative risk. In the first scenario in the U.S., there are systems and components enabled by the environment to optimally resolve the problem-set. Much of the expertise and critical decision making required to resolve the problem-set is embedded in the system. From the trauma surgeon's perspective, he/she will predictably receive the patient via EMS and then, in response to whatever stimulus the patient presents, must efficiently execute the corresponding habit pattern in conjunction with a team who shares the same mental model and relevant habit patterns within that mental model. The trauma surgeon does not need to consider how the patient gets to the hospital, what functions other human components will perform in the trauma bay, how any necessary radiographic imaging will be performed, where they will get blood products from, what to use as a light source in the operating room, etc. He/she largely just needs to execute a habit pattern in conjunction with and supported by other medical experts. Now consider the problem-set in Afghanistan. In this case there are many more frictions that might serve to increase the tOR, increase diagnostic uncertainty at any given time, and increase the risk of intervention. For starters, there are many more decision makers involved in the problem-set and many/most are not medical experts and are not working within a system expressly designed to resolve medical problem-sets. One potential consequence of this is that they don't share a mental model of the problem-set. First, a decision needs to be made by a ground force commander if the patient needs to be evacuated to medical care and when given multiple other mission related considerations. Then, other decision makers, such as a task force commander and an air mission commander, need to release a helicopter to evacuate the patient. This all takes time and may depend on multiple variables—kinetic threats, weather, other ongoing operations with competing requirements, etc. During this time, the patient may be getting hypothermic, worsening his physiologic dysfunction and shifting time terminal to an earlier point in time. Once the patient is evacuated from the mountain, he is transported to the trauma surgeon, who is located with a small surgical team and security element in a building of opportunity a short time-of-flight from the objective where the patient was injured. The surgeon and the surgical team need a plan and resources to transport the patient into their makeshift trauma bay from the helicopter, they need light to adequately assess the patient and operate, they may need imaging capability, blood, and medications beyond whatever they have with them. This may lead to other critical decisions by the trauma surgeon whether the patient should undergo surgery at the current location or be transported, at the risk of time elapsed and worsening physiological dysfunction, to a more capable facility. Ultimately, the point is that the same determinative risk (a gunshot wound to the abdomen) in the same patient can present a very different problem-set by virtue of manifesting in a different risk-context. The second scenario (in Afghanistan), which represents an adaptability risk-context, has many more degrees of freedom affecting underlying risk-variables than the first scenario (in the U.S.), which represents a predictability risk-context.

A key function of the PreDICT system is to acquire data regarding risk-context and recommend courses of action based on the effects of risk-context on the fundamental risk-variables of the problem-set: determinative risk (DR), diagnostic uncertainty (DU), interventional risk (IR), and operational risk (OR). Human decision makers require working memory (a frontal lobe function) to process different courses of action. Under optimal cognitive circumstances, humans can process four to six courses of action. Under stressful circumstances frontal lobe function and working memory is diminished. The PreDICT system can process orders of magnitude more courses of action, at machine speeds, without being compromised by the effects of mental and physical stress, cold, hunger, fatigue, etc. Essentially, the PreDICT system can rapidly generate new mental models for dynamic and/or evolving risk-contexts and recommend optimal courses of action (i.e. habit patterns) to decision makers within the time constraints of the problem-set. This allows problem-sets with multiple decision makers, especially if they are separated in time and space, to rapidly gain understanding of the problem-set and build a shared mental model. It also diminishes the risk of the liability of negative habit pattern transfer by individuals, teams, and/or systems.

The PreDICT system will function across the risk-context spectrum from predictability to adaptability risk-context. However, many of the most compelling use cases arise in adaptability risk-context scenarios where required human expertise is either deficient or absent and/or key infrastructure, such as network access, is absent or compromised and/or the situation is highly dynamic and uncertain and/or the situation is highly complex due to multiple decision makers or other factors. The PreDICT system may employ different network and computing architecture in different risk-context scenarios in order to optimize the functionality versus the employability of the technology in the different risk-context scenarios. Below, we will consider some of the different network and computing approaches that PreDICT will employ.

Embedded Application: The PreDICT system may exist as an application on a local device (such as, but not necessarily, a smartphone) and have full functionality independent of a network. The application is periodically updated, either automatically or deliberately, when the device connects to a network/cloud.

Advantages: Can function in austere environments where network capability is non-existent or in cases, such as natural or manmade disasters, where network infrastructure is compromised. This functionality is optimal for adaptability risk-context (ARC) scenarios. An important consideration in military applications is that any contemporary or future near-peer or peer on peer military conflicts will entail multi-domain operations (MDO) with a contested electromagnetic and communications spectrums and/or may entail extensive submarine, subterranean, or urban operations that challenge network and communications capabilities.

Limitations:
In the absence of a network, computing power and bandwidth is limited to the capacity of the device on which the PreDICT application is embedded at the particular time at which the PreDICT system is being employed.

Decision makers confronting problem-sets that would benefit from the PreDICT system may not have access to, or even knowledge of, the PreDICT system. For example, a layperson out jogging witnesses a fellow jogger experience cardiac arrest while trail running in an isolated wooded park. The layperson does not have the PreDICT system on their smartphone and are not aware that such capability exists. Thus, neither the patient or decision maker (the layperson) can benefit from the PreDICT system capability in this scenario if the only mechanism of employability is a device embedded application.

Caveats: In specific scenarios with controlled populations, one or both of the following approaches can be employed to decrease computing requirements. Consider the example of an infantry platoon consisting of forty Soldiers conducting a deliberate mission in enemy territory. They will employ the PreDICT system as an augmented intelligence capability for medical decision making and treatment as an application on a smartphone platform. The primary medical pathology of concern is trauma.

The population is known. Baseline physiologic, voice, motion, and other medical data for each of the forty Soldiers can be collected using the PreDICT sensor capabilities and medical records data and uploaded to the PreDICT application prior to the mission.

The most likely medical pathology to be encountered is known, trauma. The Soldiers can selectively upload and/or employ only the functionality of the application relevant to trauma pathology.

Characteristics of risk-context are known. The Soldiers can set the parameters of the PreDICT system to discount certain risk-variables in the risk-context in order to achieve more computational bandwidth at the expense of the PreDICT system having a less complete picture of the problem-set. The PreDICT system can evaluate risk-variables in the risk-context and make recommendations to the user(s) regarding the tradeoffs between potential loss of fidelity on the problem-set and gains in bandwidth and computing power. For example, a concurrent mission in another part of the area of operations (AO) may simultaneously require medical evacuation assets if Soldiers are injured on both targets. If this contingency occurs it may affect the interventions and courses of action that the PreDICT system recommends but, accounting for this contingency requires more computing power. Prior to the mission, the PreDICT system and/or the Soldiers can evaluate the probability of this contingency occurring and the consequences if it does occur and, based on these factors, consider discounting this risk-variable from the PreDICT system's decision-making calculus regarding the problem-set.

Network/Cloud Based Application: The PreDICT system may exist as a network/cloud-based application independent of any specific platform and receive input data from multiple sensors and sources and be updated in real time as the machine learning/artificial intelligence processing and analysis "learns."

Advantages: Potentiates greater computing bandwidth and power and allows all users to benefit from the most up-to-date machine learning/artificial intelligence derived from all users on the network. The network/cloud based PreDICT application can utilize any/all information available to the network to make decisions and recommendations. This is ideal for predictability risk-context scenarios such as employment within a hospital functioning within baseline parameters (e.g. electrical power and network function are operational).

Limitations: Requires an operational network and connectivity to the network.

Caveats: Some PreDICT functionality is maintained at a local device level to protect against network outages. For example, while the PreDICT system is being applied to a specific case using, for example, a smartphone as the sensor and interface, key information and "bookmarks" about the case are down-loaded on the smartphone to allow some continued PreDICT functionality regarding that specific case even if network access is lost.

Hybrid—Functionality distributed between device(s)/network(s)/cloud:

Example 1—The PreDICT processing and analytic functionality is distributed across a device with the PreDICT application, network, and cloud.

In a predictability risk-context, such as a hospital under normal conditions, this may present as a combined sensor platform-processing-analytic device, such as a smartphone with sensor capability, communicating with a network and cloud for additional data capture (such as from a medical records system) and more robust data processing and analysis.

In an adaptability risk-context, such as caring for an injured Soldier during an ongoing kinetic engagement, the fundamental relationship between device, network, and cloud may be the same but the degree of processing at each level may differ and the nature of the network and frequency of communication with other networks or the cloud may differ. For example, the device may interface with an edge computing network that may only communicate with other networks and/or the cloud at intervals, perhaps infrequently. Depending on the problem-set and associated time-constraints, these intervals may obviate drawing on the computational power of networks beyond the edge network. In such contingencies or in expectation of such contingencies, users can implement strategies for employment to decrease bandwidth requirements, such as using baseline data for potential patients/subjects as discussed above.

Example 2—The PreDICT processing and analytic functionality is distributed across multiple devices with the PreDICT application through Bluetooth or other local inter-device communications capabilities and/or across edge computing networks and/or across devices and edge computing networks.

Example 3—A device without the PreDICT application connects to a network (+/−cloud) and the device is used by the network to perform some component of the data processing and analysis. For example, a layperson with a smartphone that does not have the PreDICT application contacts an emergency network/system, such as 9-1-1. The 9-1-1 system then utilizes the device to implement PreDICT functionality. Such implementation of the PreDICT system may utilize PSAPs within the emergency network. This functionality would also exist with similar network infrastructure in secure and unsecure, classified and unclassified military, maritime, disaster or other communications networks.

Example 4—Multiple decision makers at multiple locations with different computing and connectivity resources requiring different information to make different but interdependent decisions to resolve the same problem-set.

Consider the problem-set of a hypothetical large-scale military operation with multiple units taking casualties in multiple locations. We will examine the problem-set from the perspective of three different decision makers and the computing resources required and available to them.

Decision Maker 1: A platoon medic treating a casualty during an ongoing firefight. He has a smartphone with the PreDICT application embedded. Successful resolution of the problem-set requires that the patient's injury (determinative risk) risk is mitigated and averted. This requires stabilizing (mitigating) treatment in the field followed by rapid evacuation to a surgical team.

Decision Maker 2: A taskforce commander in a joint operations center (JOC) overseeing the entire military operation. The JOC has extensive network and cloud computing capability. Successful resolution of the problem-set requires that the objective of the operation is successfully prosecuted with as few friendly deaths as possible.

Decision Maker 3: The surgical team leader at the medical facility receiving casualties from the operation. Her facility has network capabilities but not at the scale of the JOC. Successful resolution of the problem-set requires that, of the casualties sustained in the operation, her surgical team minimizes resultant morbidity and mortality.

The goals of each decision maker intersect with respect to the injured Soldier under the care of the medic—they all want the Soldier to live. But, they all need different information at any given time and all have different resources to process and analyze that information.

Decision Maker 1 requires specific information about the patient's condition and information about when the medical evacuation MEDEVAC) helicopter will arrive in order to optimally mitigate the injuries and associated risk over a known period of time.

Decision Maker 2 needs to know the risk (consequence and probability) and time-constraint on that risk (i.e. what is the probability the patient will die and when) on every casualty in the battlespace and then needs to allocate MEDEVAC assets accordingly. He also needs to know what other high-risk engagements are ongoing. He doesn't need granular details about any patients' medical condition.

Decision Maker 3 needs to how many casualties are in the battlespace, needs accurate but not granular details on their medical status, needs to know when each patient will be arriving, and needs a general understanding of the phase of the operation—is it over or will it be ongoing for another twelve hours with the potential to produce many more casualties. This allows the surgical team and facility to optimally prepare and sequence resources and capabilities.

Decision Maker 1 only requires the computing capability for the PreDICT system to process and analyze data on his single patient. Other key information, such as when the MEDVAC helicopter will arrive can be computed on the PreDICT system at the JOC level and pushed to his PreDICT platform over a communications network.

Decision Maker 2 has adequate computing capability to process and analyze all incoming data. However, the PreDICT capability being employed by the medic only needs to push the data required for the commander/JOC level PreDICT system to solve the MEDEVAC allocation versus total casualties in the battlespace problem-set.

Decision Maker 3 has intermediate computing capability and also has different information requirements that are a hybrid of information at the level of all medics in the battlespace and the JOC. She needs to know how many patients require what resources and when and the probability of future resource requirements. The PreDICT capability at her location can receive only this relevant information to ensure that the network has sufficient local processing and analytic capability to determine optimal resource allocation and sequencing.

SUMMARY

The time-constrained, future value, optimal stopping problem model described above demonstrates both a functionality of the PreDICT system and a type of problem-set that the PreDICT system will resolve. The discussion of risk-context is intended to illustrate the range of complexities that decision makers may confront in resolving a problem-set and how a range of problem-sets can exist even for the same underlying determinative risk (DR).

In both the functionality of the PreDICT system and in the realities of the human and physical world the quantitative model described above is more complex than described here for the purposes of illustration and conceptual understanding. From the standpoint of PreDICT functionality and reality, possibility-sets resolve into probability-sets which ultimately resolve into problem-sets, often in a dynamic, non-linear fashion. Thus, the model examined above is playing out multiple times in parallel and serial with forward and backward equilibrium between possibilities, probabilities, and phases and risk-variables within the model until an outcome is reached; either in the form of the DR being mitigated or averted or in the form of the terminal outcome being realized at time terminal. Furthermore, if a calculation of relative benefit (RB(t)) is desired out to a time beyond tT' or tR, the model will effectively re-set and reapply to the new problem-set. There are also some assumptions in the model as presented above that are accounted for in the functionality of the PreDICT system. For example, in the model, interventional risk (IR) is accounted for once the intervention is complete. In reality, interventions (both diagnostic and therapeutic) impart risk prior to completion and have variable levels of risk during implementation and after completion that may or may not extinguish at some future time. The PreDICT system can account for this.

Another important concept examined above is that of "time-constraint." There are periods of time of sufficiently short duration that most humans would agree that they present a time-constraint for resolving any problem-set within them. Furthermore, there may be a clear time-constraints on a problem-set that, while relatively long in duration, nonetheless represents a time-constraint, such as a deadline. With respect to the PreDICT system and the time-constrained problem-sets under discussion, those categories of time-constraints apply. However, what is also applicable is the concept of "risk-density"—the time-constraint (or potential time-constraint) established by the underlying determinative risk relative to the time of operational risk (tOR) required to mitigate or avert the determinative risk. In other words, how much time is afforded by the problem-set relative to the amount of time required to resolve the problem-set. At a fundamental level, with respect to time-constrained problem-sets, the function of the PreDICT system is to decrease the risk-density of time by decreasing tOR and the associated interventional risk required to ultimately mitigate or avert the DR within tOR.

Specific benefits and capabilities of the PreDICT system, relative to the model described above, are listed below. The PreDICT system achieves these capabilities by using various data inputs, processing, and analysis to elucidate patterns and indicators that are below and/or outside the threshold of human sensory capabilities and cognition at superhuman speeds and capacity. These include patterns and indicators, including capabilities, limitations, and constraints, at all levels of the problem-set to include the determinative risk and the risk-context and its three domains; environment, systems, and components.

Rapidly recognize and differentiate a problem-set from a possibility-set and probability-set resulting in an earlier time of meaningful contact (tMC). Essentially, it can recognize that a problem-set exists earlier and define that problem-set earlier than human sensory and cognitive capabilities.

Increase both the time and risk efficiency of attaining diagnostic certainty and/or the diagnostic certainty threshold:
  Rapidly attain a diagnostic certainty threshold (tDx) and/or markedly improve the ratio of diagnostic certainty relative to time. The PreDICT system can achieve an equal or higher level of diagnostic certainty in less time than humans are capable of.
  Rapidly achieve diagnostic certainty threshold (tDx) and/or markedly improve the ratio of diagnostic certainty relative to time with less interventional risk (IR) through the use of non-contact and minimal-contact sensors and data acquisition. The PreDICT system can achieve a higher level of diagnostic certainty with less interventional risk than current standards-of-care by requiring less invasive or risk-bearing diagnostic interventions.

Decrease the time to the decision to act (tDA) and the risk appropriateness of the decision to act by evaluating the risk-benefit of potential interventions (including inaction) for the determinative risk (DR) in the risk-context and by providing recommendations on the optimal sequencing and logistics of interventions in the risk-context.

Decrease the time to intervention (tI) and relative risk of therapeutic intervention by computing and recommending or enacting the most efficient intervention course(s) of action for the determinative risk in the risk-context.

Decrease the time to intervention efficacy (tIE) by calculating tIE as a component of recommended interventions.

Decrease time of operational risk (tOR) by decreasing the time and risk efficiency of its additive components: tMC, tDx, tDA, tI, tIE. The PreDICT capability can function or be employed at multiple levels to decrease one, some, or all of these components.

Enhance Adaptability:
  Non-Experts: The PreDICT system creates a "mental model" of the problem-set and recommends interventions and courses of action. Non-experts, by definition, do not have well developed mental models or habit patterns in their area of non-expertise. The PreDICT system effectively provides a level of task-specific and operational expertise to non-expert decision makers.
  Experts: The PreDICT system creates a "mental model" of the problem-set and recommends interventions and courses of action. Experts have well developed mental models and habit patterns. This makes them susceptible to the risk of the liability of negative habit pattern transfer in novel problem-sets with similar or identical cues and stimuli to familiar problem-sets. In such cases, experts may apply mental models and, in turn, habit patterns, based on prior experience that do not optimally align with the reality of the novel problem-set. While experts in such novel problem-sets may have most or all of the required task-specific expertise to mitigate or avert the determinative risk they may lack the relevant operational expertise to optimally apply their task-specific expertise in the novel risk-context. The PreDICT system effectively provides experts with operational expertise by providing a rapidly updated mental model and recommendations on interventions and courses of action to potentiate the optimal application of their task-specific expertise.

Groups: In many cases, problem-sets require multiple simultaneous decision makers. In order for decision makers to optimally resolve the problem-set they require a shared and accurate mental model. This is difficult to achieve in complex, rapidly emerging, time constrained problem-sets, particularly if decision makers are separated in time and/or space and/or do not have access to the same information and/or a similar ability to interpret the information. The PreDICT system provides multiple decision makers, including those separated in time and/or space, with the same information and interpretation of that information to create a shared and accurate mental model and recommendations for interventions and courses of action.

The model discussed above was developed through the lens of medical determinative risk in high-consequence, dynamic, austere risk-contexts. However, this model applies across multiple human decision-making domains outside of both medicine and the risk-contexts where it was conceived. It applies whenever a decision maker confronts a potential or actual determinative risk which will, unavoidably, manifest in some risk-context and present a problem-set. The PreDICT system provides an augmented intelligence capability through the use of multiple sensors and data acquisition streams to acquire, process, and analyze information both "down and in" (the determinative risk) and "up and out" (the risk-context) and provide optimal recommendations to decision makers. Beyond the PreDICT system's medical capability and functionality there are multiple other applications, some (but not all) of which are illustrated in the use and dual-use cases section of this document.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method for use in medical evaluation of a time constrained critical illness or injury (TCCI) condition of a subject, comprising:
   obtaining input data regarding said TCCI condition of said subject, said input data related to one or more physiological, anatomical, or pathological parameters of said subject, said input data based on sensor information acquired via a mobile device;
   providing said input data to a processing system including a machine learning module to determine evaluation information including at least one of diagnostic evaluation data and risk stratification data, wherein said processing platform is operative for preprocessing said sensor data for use by said machine learning module, said preprocessing comprising using motion microscopy to generate at least a portion of said input data, said processing system further being operative to generate, based on said evaluation information, output information including intervention information describing a course of treatment for said subject; and
   outputting, at a user device, the same as or different than said mobile device, said output information for use in treating said TCCI condition of said subject.

2. The method as set forth in claim 1, wherein said collecting data comprises obtaining non-contact data collected free from contact between said subject and said sensor system.

3. The method as set forth in claim 2, wherein said input data comprises imaging data.

4. The method as set forth in claim 3, wherein said imaging data is obtained by one or more of an autonomous imaging device, a WebCam, a smart phone or tablet camera, a wearable camera, a red-blue green (RBG) camera and an infrared thermography (IRT) imaging system.

5. The method as set forth in claim 2, wherein said non-contact data comprises audio information.

6. The method as set forth in claim 5, wherein said audio information includes information indicative of vocal biomarkers or key words or phrases.

7. The method as set forth in claim 1, wherein said collecting data comprises obtaining contact information involving contact between said subject a said sensor system.

8. The method as set forth in claim 7, wherein said contact information comprises sensor information for use in evaluating one of fine motor coordination, gross motor characteristics, or the acceleration or deceleration of a subject.

9. The method as set forth in claim 7, wherein said contact information is obtained by a wearable monitoring device.

10. The method as set forth in claim 1, wherein said input data comprises medical record data.

11. The method as set forth in claim 10, wherein said medical record data relates to one of medical history data, physical exam data, diagnostic studies data, diagnosis data, disposition data, and outcome data.

12. The method as set forth in claim 1, wherein said machine learning module implements an unsupervised process for one of dimensionality reduction and data clustering.

13. The method as set forth in claim 1, wherein said machine learning module implements a supervised process for developing correlations between different categories of input data.

14. The method as set forth in claim 1, wherein said machine learning module is operative for developing diagnostic models for input data subsets for each of multiple investigational phenotypes.

15. The method as set forth in claim 1, wherein said machine learning module is operative to determine noncontact vital signs of said subject, said noncontact vital signs including one or more of the following: temperature, heart rate, respiratory rate, blood pressure, blood oxygen saturation (SPO2), tissue oxygen saturation (STO2), and variability thereof.

16. The method as set forth in claim 1, wherein said output information relates to the presence or absence of an illness or injury.

17. The method as set forth in claim 1, wherein said output information includes information concerning an appropriate diagnostic or therapeutic course of action.

18. A system for use in medical evaluation of a time constrained critical illness or injury (TCCI) condition of a subject, comprising:
  an input device for collecting information regarding said TCCI condition of said subject, said input device being operatively associated with a sensor system to obtain sensor data related to one or more physiological, anatomical, or pathological parameters of said subject, said input device comprising a mobile device;
  said input device including input device logic for processing said sensor data and providing said sensor data to a processing system including a machine learning module to determine evaluation information including at least one of diagnostic evaluation data and risk stratification data, wherein said processing platform is operative for preprocessing said sensor data to provide input data for use by said machine learning module, said preprocessing comprising using motion microscopy to generate at least a portion of said input data, said processing system further being operative to generate, based on said evaluation information, output information including intervention information concerning a course of treatment for said subject; and
  a user device, the same as or different than said mobile device, including user device logic operative for processing, at said user device, said output information to provide an output for use in treating said TCCI condition of said subject.

19. The system as set forth in claim 18, wherein said input device is operative for obtaining non-contact data collected free from contact between said subject and said sensor system.

20. The system as set forth in claim 19, wherein said input device is operative to provide imaging information.

21. The system as set forth in claim 19, wherein said input device is operative to collect audio information.

22. The system as set forth in claim 18, wherein said input device is operative to obtain contact information based on contact between said subject and said sensor system.

23. The system as set forth in claim 22, wherein said contact information comprises a sensor for evaluating one of fine motor coordination, gross motor characteristics, or the acceleration or deceleration of a subject.

24. The system as set forth in claim 22, wherein said contact information is obtained by a wearable monitoring device.

25. The system as set forth in claim 18, wherein said input device is operative for obtaining medical record data.

26. The system as set forth in claim 18, wherein said machine learning module implements an unsupervised process for one of dimensionality reduction and data clustering.

27. The method as set forth in claim 18, wherein said machine learning module implements a supervised process for developing correlations between different categories of input data.

28. The system as set forth in claim 18, wherein said machine learning module is operative for developing diagnostic models for input data subsets for each of multiple investigational phenotypes.

29. The system as set forth in claim 18, wherein said machine learning module is operative to determine noncontact vital signs of said subject, said noncontact vital signs including one or more of the following: temperature, heart rate, respiratory rate, blood pressure, blood oxygen saturation (5PO2), tissue oxygen saturation (STO2), and variability thereof.

30. The system as set forth in claim 18, wherein said output information relates to the presence or absence of an illness or injury.

31. The system as set forth in claim 18, wherein said output information includes information concerning an appropriate diagnostic or therapeutic course of action.

* * * * *